US012779125B2

(12) United States Patent
Doubet et al.

(10) Patent No.: US 12,779,125 B2
(45) Date of Patent: Nov. 3, 2026

(54) CONTAINER ADAPTER FOR REMOVABLY ATTACHABLE SYRINGE

(71) Applicants: Paul D. Doubet, Farmington, IL (US); James T. Doubet, Parker, CO (US)

(72) Inventors: Paul D. Doubet, Farmington, IL (US); James T. Doubet, Parker, CO (US)

( * ) Notice: Subject to any disclaimer, the term of this patent is extended or adjusted under 35 U.S.C. 154(b) by 107 days.

(21) Appl. No.: 17/387,057

(22) Filed: Jul. 28, 2021

(65) Prior Publication Data

US 2021/0353863 A1 Nov. 18, 2021

Related U.S. Application Data

(62) Division of application No. 16/858,686, filed on Apr. 26, 2020, now Pat. No. 11,103,641.

(51) Int. Cl.
*A61M 5/24* (2006.01)
*A61J 1/20* (2006.01)

(52) U.S. Cl.
CPC .......... *A61M 5/2455* (2013.01); *A61J 1/2096* (2013.01); *A61M 2005/2444* (2013.01); (Continued)

(58) Field of Classification Search
CPC .......... A61J 1/20; A61J 1/2096; A61J 1/2003; A61J 1/2006; A61J 1/201; A61J 1/2013; (Continued)

(56) References Cited

U.S. PATENT DOCUMENTS 5,279,576 A * 1/1994 Loo ........................ A61J 1/2096 222/1
5,344,404 A 9/1994 Benson
(Continued)

FOREIGN PATENT DOCUMENTS

EP 0499481 A1 2/1992
WO 2017091643 A1 6/2017

OTHER PUBLICATIONS

In re Paul D. Doubet, et al., U.S. Appl. No. 16/858,686, filed Apr. 26, 2020, Office Action, Jul. 1, 2020, 13 pages.
(Continued)

*Primary Examiner* — Kevin C Sirmons
*Assistant Examiner* — Leah J Swanson
(74) *Attorney, Agent, or Firm* — Marcia L. Doubet

(57) ABSTRACT

Apparatus for removably attaching a syringe to a container for extracting fluid therefrom into the syringe, which is particularly beneficial for fluid having a relatively high viscosity. The disclosed container adapter holds a syringe adapter securely therein (the syringe adapter configured for providing a fluid path between a container and a syringe) while also securing the syringe adapter to the container, and provides an attachment point for securely attaching the syringe to the syringe adapter and thus to the container (at least) while the fluid is withdrawn from the container into the syringe. The syringe is removably attached to an end of the syringe adapter during the withdrawal, and a cap is provided that closes entry and exit to this attachment point when the syringe is not in place. The cap preferably attaches to the syringe adapter using a connection that mimics the connection used by the syringe.

20 Claims, 28 Drawing Sheets

(52) U.S. Cl.
CPC ................. *A61M 2005/247* (2013.01); *A61M 2005/2488* (2013.01)

(58) Field of Classification Search
CPC ........ A61J 1/2017; A61J 1/202; A61J 1/2024; A61J 1/2027; A61J 1/2031; A61J 1/2034; A61J 1/2037; A61J 1/2041; A61J 1/2044; A61J 1/2048; A61J 1/2051; A61J 1/2055; A61J 1/2058; A61J 1/2062; A61J 1/2065; A61J 1/2068; A61J 1/2072; A61J 1/2075; A61J 1/2079; A61J 1/2082; A61J 1/2086; A61J 1/2089; A61J 1/2093; A61J 1/22; A61M 5/2455; A61M 2005/2444; A61M 2005/247; A61M 2005/2488
See application file for complete search history.

(56) References Cited

U.S. PATENT DOCUMENTS

| | | | | |
|---|---|---|---|---|
| 5,413,561 | A * | 5/1995 | Fischell ................ | A61M 39/20 604/167.01 |
| 5,776,124 | A * | 7/1998 | Wald ..................... | A61J 1/2096 604/403 |
| 5,924,584 | A | 7/1999 | Hellstrom et al. | |
| 8,752,598 | B2 * | 6/2014 | Denenburg ........... | A61J 1/2096 141/105 |
| 8,827,977 | B2 | 9/2014 | Fangrow | |
| 8,985,162 | B2 | 3/2015 | Aneas | |
| 9,510,997 | B2 | 12/2016 | Kriheli et al. | |
| 9,801,788 | B2 * | 10/2017 | Banik ................... | A61J 1/1412 |
| 10,426,703 | B2 | 10/2019 | Russo et al. | |
| 10,709,850 | B2 | 7/2020 | Doubet et al. | |
| 11,071,834 | B2 | 7/2021 | Doubet et al. | |
| 11,090,444 | B2 | 8/2021 | Doubet et al. | |
| 11,097,058 | B2 | 8/2021 | Doubet et al. | |
| 11,103,641 | B1 | 8/2021 | Doubet et al. | |
| 11,173,257 | B2 | 11/2021 | Doubet | |
| D950,718 | S | 5/2022 | Doubet et al. | |
| 11,337,894 | B2 | 5/2022 | Doubet et al. | |
| 11,446,450 | B2 | 9/2022 | Doubet et al. | |
| 11,707,579 | B2 | 7/2023 | Doubet et al. | |
| 2002/0127150 | A1 * | 9/2002 | Sasso .................... | A61J 1/2096 422/569 |
| 2003/0079314 | A1 | 5/2003 | Yeh | |
| 2005/0159724 | A1 | 7/2005 | Enerson | |
| 2008/0015539 | A1 | 1/2008 | Pieroni et al. | |
| 2009/0120934 | A1 | 5/2009 | Domkowski | |
| 2009/0177177 | A1 * | 7/2009 | Zinger .................. | A61J 1/2096 604/414 |
| 2012/0184938 | A1 * | 7/2012 | Lev ...................... | B65D 51/002 604/414 |
| 2012/0220978 | A1 * | 8/2012 | Lev ...................... | A61J 1/2096 604/414 |
| 2012/0265163 | A1 | 10/2012 | Cheng et al. | |
| 2012/0296307 | A1 * | 11/2012 | Holt ...................... | A61J 1/2051 604/407 |
| 2013/0331810 | A1 | 12/2013 | Bazala et al. | |
| 2016/0015601 | A1 * | 1/2016 | Davidson .............. | A61J 1/2096 604/403 |
| 2017/0065486 | A1 * | 3/2017 | Mosler .................. | A61J 1/2013 |
| 2018/0050183 | A1 | 2/2018 | Taylor | |
| 2018/0104150 | A1 | 4/2018 | Dubaele et al. | |
| 2018/0161243 | A1 * | 6/2018 | Ariagno ................ | A61J 1/2082 |
| 2018/0344570 | A1 * | 12/2018 | Davis .................... | A61J 1/1425 |
| 2019/0060171 | A1 | 2/2019 | Lee | |
| 2019/0380911 | A1 | 12/2019 | Doubet | |
| 2019/0388625 | A1 | 12/2019 | Doubet et al. | |
| 2020/0368106 | A1 | 11/2020 | Eicke | |
| 2020/0405978 | A1 | 12/2020 | Doubet et al. | |

OTHER PUBLICATIONS

In re Paul D. Doubet, et al., U.S. Appl. No. 16/858,686, filed Apr. 26, 2020, Office Action, Oct. 20, 2020, 20 pages.
In re Paul D. Doubet, et al., U.S. Appl. No. 16/858,686, filed Apr. 26, 2020, Office Action, Feb. 17, 2021, 26 pages.
In re Paul D. Doubet, et al., U.S. Appl. No. 16/858,686, filed Apr. 26, 2020, Notice of Allowance, May 21, 2021, 11 pages.
PCT Application PCT/US2021/029019, International Search Report dated Aug. 26, 2021 (2 pages).
PCT Application PCT/US2021/029019, Written Opinion of the International Searching Authority dated Aug. 26, 2021 (9 pages).
Chug Cap (TKWide), Klean Kanteen, printed from Internet location https://www.mukama.com/en/klean-kanteen-chug-cap-tkwide (year 2022), 2 pages.
Water Bottle Sport Caps (WBSC), bottles.com, printed from Internet location https://www.ebottles.com/showcap-familyid-1456-kw-WATER_BOTTLE_SPORT_CAPS.htm (year 2022), 2 pages.
PCT Application PCT/US2021/029019, International Preliminary Report on Patentability dated Nov. 10, 2022 (11 pages).

* cited by examiner

SECTION A-A

DETAIL B

SECTION C-C

DETAIL D

SECTION E-E

DETAIL F

SECTION G-G

DETAIL H

SECTION J-J

DETAIL K

SECTION L-L

DETAIL M

SECTION N-N

DETAIL P

SECTION R-R

DETAIL T

CONTAINER ADAPTER FOR REMOVABLY ATTACHABLE SYRINGE

BACKGROUND

The present invention relates to improved apparatus for removably attaching a syringe to a container (such as a bottle) for use with extracting fluid from the container into the syringe, and method(s) of using same, and is particularly advantageous for higher-viscosity fluid.

Withdrawing fluid from a container into a syringe can be cumbersome and/or tedious for a person having that task, particularly when the fluid is viscous and therefore requires a relatively long draw time (as compared to a thinner fluid).

BRIEF SUMMARY

The present invention is directed to improved apparatus for removably attaching a syringe to a container for use with extracting fluid from the container into the syringe, and method(s) of using same, and is particularly advantageous for higher-viscosity fluid. In one aspect, this comprises a container adapter that further comprises: a syringe adapter comprising a sidewall extending between a proximal end and a distal end opposite the proximal end, the sidewall having an interior surface defining a chamber, the sidewall defining a proximal-end opening and a distal-end opening at a terminal end of the proximal end and the distal end, respectively, the proximal end configured to be removably connected to a syringe tip at a distal end of a syringe; a component configured for securely holding the syringe adapter therein; and a cap. In this aspect, the component is configured to hold the syringe adapter such that the distal end of the syringe adapter extends outward from a bottom of the component while the proximal end of the syringe adapter extends outward from a top of the component, the component being further configured for securely attaching over a collar on a neck opening of a container and to thereby hold the distal end of the syringe adapter within an interior of the container, the interior of the container holding a fluid therein. In this aspect, the cap is configured to removably connect to the proximal end of the syringe adapter and thereby close off a proximal-end opening into the chamber of the syringe adapter, the cap further configured to be disconnected from the proximal end of the syringe adapter for removably connecting the syringe tip thereto to thereby open the proximal-end opening into the chamber to open a fluid path between a barrel of the syringe, the chamber of the syringe adapter, the distal-end opening, and the fluid-containing interior of the container. Preferably, the cap connects to the proximal end of the syringe adapter using a secure, Luer-type lock connection that is made by rotating a flanged area extending laterally from the proximal end of the syringe adapter within corresponding internal threads of a threaded area in the cap, the flanged area also configured for making the secure, Luer-type lock connection with the syringe tip of the syringe. Preferably in this aspect, the component further comprises a sidewall connected to, and extending between, the top of the component and the bottom of the component, the bottom of the component further comprising a lip area extending therefrom; the component is configured to hold the syringe adapter by configuring the top of the component to separate along a center thereof, thereby exposing an opening in the top that is configured to surround an outer surface of at least a portion of the syringe adapter sidewall; the component is configured to attach over the collar by surrounding an exterior of the collar with an interior of the component and causing the lip area to hook underneath a lower edge of the collar; and the component is further configured to close around the portion of the outer surface of the syringe adapter sidewall and the collar, and to stay closed. Preferably, the component further comprises a strap extending from an area at a first end of the sidewall of the component and an extension from an area at a second end of the sidewall of the component, the extension having an opening therein, such that the component is configured to stay closed by inserting a loose end of the strap through the extension until the component is no longer separated along the center thereof, the loose end configured with at least one protrusion that prevents the strap from being backed out of the opening in the extension. (Rather than the opening in the top being closeable to then surround the portion of the outer surface of the syringe adapter sidewall, in an alternative approach, some portion of the outer surface of the syringe adapter sidewall is molded to a side of the opening, such that closing the top then fully surrounds the outer surface of at least the portion of the syringe adapter sidewall.)

In another aspect, a container adapter for use with extracting fluid from a container and into a syringe comprises a component configured for securely attaching a syringe adapter to a container, the component having a cap securely attached thereto. In this aspect, the syringe adapter comprises a sidewall extending between a proximal end and a distal end opposite the proximal end, the sidewall having an interior surface defining a chamber, the sidewall defining a proximal-end opening and a distal-end opening at a terminal end of the proximal end and the distal end, respectively, the proximal end configured to be removably connected to a syringe tip at a distal end of a syringe; the syringe adapter is preferably molded to the component such that the distal end of the syringe adapter extends outward from a bottom of the component while the proximal end of the syringe adapter extends outward from a top of the component; the component is configured with a plurality of sides that are separated from one another, at and towards a terminal end, by a gap, each of the sides being fixedly connected to the top of the component at an edge opposite the terminal end and being able to flex/bend slightly outward at the terminal end, each of the terminal ends further comprising a lip area extending therefrom; and the component is further configured for securely attaching over a collar on a neck opening of a container and to thereby hold the distal end of the syringe adapter within an interior of the container, the interior of the container holding a fluid therein. In this aspect, the cap is configured to removably connect to the proximal end of the syringe adapter and thereby close off the proximal-end opening into the chamber of the syringe adapter, the cap further configured to be disconnected from the proximal end of the syringe adapter for removably connecting a distal end of the syringe thereto to thereby open the proximal-end opening into the chamber to open a fluid path between a barrel of the syringe, the chamber of the syringe adapter, the distal-end opening of the syringe adapter, and the fluid-containing interior of the container. Preferably, the component of this aspect is configured to securely attach over the collar by forcing (e.g., by pushing) the component over an exterior of the collar and thereby causing the sides of the component to flex/bend outward around the exterior of the collar until the exterior of the collar is enclosed within an interior of the component and the lip area reaches a lower edge of the collar and hooks underneath the lower edge. In an alternative approach, the component is configured with an opening into which the syringe adapter is insertable, instead of the syringe adapter being molded to the component.

In a further aspect, a method of removably attaching a syringe to a container for withdrawing fluid from the container into the syringe comprises: inserting a distal end of a syringe adapter into a through-hole opening of a stopper to thereby attach the syringe adapter to the stopper, the syringe adapter comprising a sidewall extending between a proximal end and the distal end, the proximal end being opposite the distal end, the sidewall having an interior surface defining a chamber, the sidewall defining a proximal-end opening and a distal-end opening at a terminal end of the proximal end and the distal end, respectively, the proximal end configured to be removably connected to a syringe tip at a distal end of a syringe; inserting at least a lower portion of the stopper into a neck opening of the container, the stopper sized so as to plug the neck opening with the lower portion of the stopper while causing an upper portion of the stopper to rest upon an upper surface of the neck opening, while enabling the distal end of the attached syringe adapter to extend into an interior of the container, the interior of the container holding a fluid therein; placing a component over the proximal end of the syringe adapter, the attached stopper, and an outer surface of the neck opening and then making a secure attachment therebetween, the component comprising a sidewall connecting a top side and a bottom side thereof, the top side configured with an opening sized to accommodate a diameter of the proximal end of the syringe adapter and the bottom side configured with an opening sized to accommodate a larger of a diameter of an extension that extends laterally from the syringe adapter and a diameter of the outer surface of the neck opening, the sidewall of the component defining a chamber having a diameter sized to surround the diameter of the extension and the diameter of the outer surface of the neck opening and having a height sized to extend over the extension, the upper portion of the stopper, and the outer surface of the neck opening; attaching a cap to the syringe adapter, the cap being attached to a first terminal end of a lanyard, the lanyard having a ring attached thereto at a second terminal end, the attaching further comprising placing the ring around at least a portion of an outer surface of the syringe adapter sidewall; removably connecting the cap to the proximal end of the syringe adapter to thereby close off the proximal-end opening into the chamber of the syringe adapter; and disconnecting the cap from the proximal end of the syringe adapter and then removably connecting the syringe tip to the proximal end of the syringe adapter, thereby opening the proximal-end opening into the chamber to open a fluid path between a barrel of the syringe, the chamber of the syringe adapter, the distal-end opening of the syringe adapter, and the fluid-containing interior of the container. In this aspect, removably connecting the cap preferably comprises rotating a flanged area extending laterally from the proximal end of the syringe adapter within corresponding internal threads of a threaded area in the cap and removably connecting the syringe preferably comprises rotating the flanged area within corresponding internal threads of a threaded area in the syringe tip; the attaching preferably further comprises placing the ring within an indentation in the portion of the outer surface of the syringe adapter sidewall; and making the secure attachment preferably further comprises crimping the component to cause an edge of the opening in the bottom side of the sidewall of the component to lock in place under a bottom edge of the outer surface of the neck opening.

Various embodiments of these and other aspects of the present invention may be provided in view of the present disclosure. It should be noted that the foregoing is a summary and thus contains, by necessity, simplifications, generalizations, and omissions of detail; consequently, those of ordinary skill in the art will appreciate that the summary is illustrative only and is not intended to be in any way limiting. Other aspects, inventive features, and advantages of the present invention, as defined by the appended claims, will become apparent in the non-limiting detailed description set forth below.

BRIEF DESCRIPTION OF THE SEVERAL VIEWS OF THE DRAWINGS

The present invention will be described with reference to the following drawings, in which like reference numbers denote the same element throughout.

DETAILED DESCRIPTION

Figure 1:
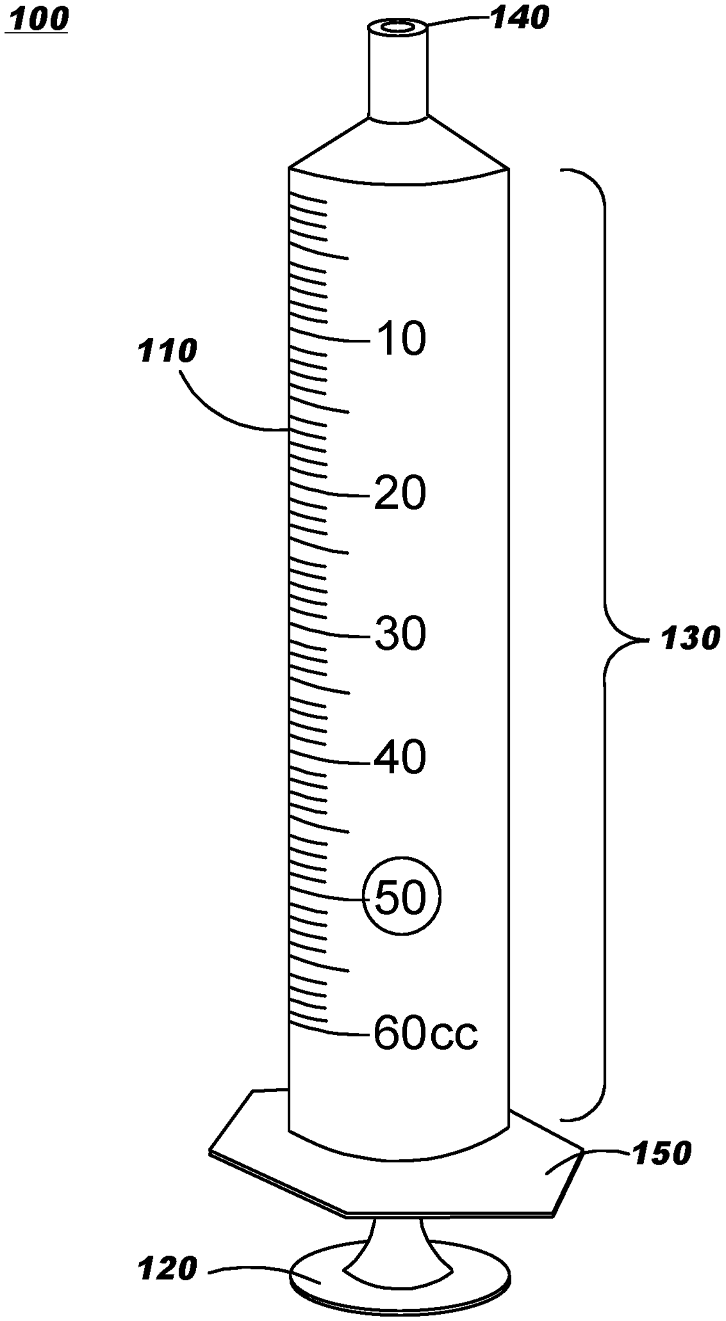
FIG. 1 (Prior Art)
FIGS. 1-3 depict examples of prior art syringes.

As noted earlier, withdrawing fluid from a container (such as a bottle) into a syringe can be cumbersome and/or tedious for a person having that task, particularly when the fluid is viscous and therefore requires a relatively long draw time (as compared to a thinner fluid). Embodiments of the present invention are directed toward a "container adapter", which as will become evident in view of the detailed descriptions below, is designed to provide an improved experience for the person withdrawing fluid from a container. The container adapter attaches to a container, and is directed toward securely holding a device referred to herein as a "syringe adapter" (where the syringe adapter device is configured for providing a fluid path between a container and a syringe) and thereby also securing the syringe adapter to the container. By holding the syringe adapter securely to the container, the container adapter thereby provides an attachment point for a syringe—that is, when the syringe is attached to the syringe adapter held within the container adapter, the syringe is thereby securely attached to the container (at least) while the fluid is being withdrawn from the container, through the syringe adapter, and into the syringe. Due to this assembly, the user has fewer individual components to hold onto and manage during the withdrawal process. The user may therefore be less likely to experience problems while withdrawing fluid—including, but not limited to, accidentally dropping the container of fluid, which could enable its (potentially-expensive) contents to leak out and thereby be wasted.

Embodiments of the disclosed container adapter enable attaching a syringe adapter (which is discussed in further detail herein) to a container of fluid in a permanent (or semi-permanent) manner, such that a distal end of the syringe adapter is held within the body (i.e., interior) of the container and a proximal end of the syringe adapter extends outward from the container. The syringe adapter has a hollow chamber (i.e., a hollow body), and thus has an opening at its distal end and an opening at its proximal end. The container adapter is designed to hold the syringe adapter such that the distal end of the syringe adapter extends into the container, providing a path for the fluid to enter into the hollow chamber through the opening in the distal end of the syringe adapter. A cap of the container adapter is used to close off entry into the opening at the proximal end of the hollow chamber of the syringe adapter when fluid is not being withdrawn from the container. When it is desired to withdraw fluid from the container, the cap is opened, enabling the distal end of a syringe to be attached to the proximal end of the syringe adapter, the proximal end of the syringe adapter being configured for making a secure connection with the distal end of the syringe. More particularly, the attachment between the syringe and the syringe adapter connects the proximal end of the syringe adapter to a syringe tip located at the distal end of the syringe. Once the syringe is in place on the syringe adapter, fluid can be withdrawn from the container, through the distal end opening and into the hollow chamber of the syringe adapter, and then through the proximal end opening and through an opening in the syringe tip and finally into the syringe barrel. (As will be readily understood, the syringe tip at the distal end of the syringe has an opening therein; accordingly, as the fluid exits the hollow chamber, it passes through the proximal-end opening of the syringe adapter and also through the distal-end opening in the syringe tip of the attached syringe.) After withdrawing the desired amount of fluid, the syringe is preferably detached from the syringe adapter (which remains attached, by the container adapter, to the container), and the cap is replaced to close off the opening at the proximal end of the syringe adapter. (As will be obvious from teachings herein, it is not required that the syringe is detached from the syringe adapter within any particular time limit, and the detachment may thus occur at the convenience of the user. Similarly, it is not required that the withdrawal commence within any particular time period after attachment of the syringe to the syringe adapter. Accordingly, it is noted herein that the container adapter secures the syringe to the syringe adapter—and thereby to the container—"at least" while fluid is being withdrawn, and discussions herein of attaching the syringe while fluid is being withdrawn should therefore be construed as signifying "at least" while fluid is being withdrawn.)

U.S. patent application Ser. Nos. 16/010,155, 16/166,111, 16/203,858, 16/393,696, 16/563,896, and 16/698,471 (hereinafter, "the related applications") disclose various embodiments of a device referred to therein as a "syringe adapter", and teachings thereof are hereby incorporated herein by reference. These various embodiments are directed toward improved syringeability for viscous fluids, and more particularly, toward reducing the time (and effort) required to draw viscous fluid into a syringe. Generally stated, an embodiment of a syringe adapter, as disclosed in at least one of the related applications, comprises a sidewall extending between a proximal end and a distal end opposite the proximal end, the sidewall having an interior surface defining a chamber, the proximal end configured to be connected to a syringe while withdrawing fluid from a container through the chamber and into a barrel of the syringe and the distal end configured for inserting into the container for the withdrawal, wherein an opening at the distal end is relatively large in diameter to facilitate withdrawing fluid having a relatively high viscosity. The related applications describe various issues pertaining to withdrawing viscous fluid from a container prior to the invention of the syringe adapter, and describe significant advantages provided by the disclosed syringe adapter in its various embodiments. Reference may be made to the related applications for detailed information regarding those issues and advantages, and accordingly, those descriptions are not repeated fully herein.

An embodiment of the present invention may be advantageously used with a syringe adapter as disclosed in the related applications, in view of disclosures provided herein, to further facilitate withdrawing viscous fluid from a container. (For ease of reference, discussions herein refer to using an embodiment of the syringe adapter as disclosed in the related applications, although this is by way of illustration but not of limitation. For example, while the related applications disclose that an opening into the distal end of the syringe adapter is preferably on the order of approximately 0.10 inches in diameter, with other ranges for this diameter also disclosed therein, it is noted that an embodiment of the present invention may be used advantageously for holding a syringe adapter that has a different opening size and/or feature(s) that differ from those of the syringe adapter disclosed in the related applications.)

Discussions are presented herein primarily with reference to fluid that comprises a medication of some sort; this is by way of illustration and not of limitation, however, and it should be noted that the disclosed container adapter may be beneficial for use with a container that holds fluid without regard to the purpose of the fluid. Discussions presented herein also refer primarily to fluids that are viscous—that is, fluids having a relatively high viscosity—although this is also by way of illustration and not of limitation, and it should be noted that the disclosed container adapter may be beneficial for use with a container that holds fluid without regard to the viscosity of the fluid.

Fluids may vary widely in their viscosity, depending upon their chemical formulation. Viscosity is sometimes defined as the resistance of a substance to flow. The viscosity of water is relatively low, for example, while the viscosity of honey is relatively high. The viscosity of some substances can be changed by applying heat; for example, melting butter increases its ability to flow. Some fluids (including fluid medications) may have a viscosity that is relatively low and is similar to that of water, for example, and thus will flow quite easily, while other fluids (including fluid medications) are known that have a viscosity that is markedly different from water.

Fluid medications intended for use with animals are commonly marketed in multi-dose packaging, such as bottles that hold enough fluid for administering several doses. A bottle of medication might hold 500 milliliters, for example (equivalently, 500 cubic centimeters), which is roughly equivalent to 16.9 ounces. The bottle might be made of glass or plastic, and a container having a configuration other than a bottle might be used. The term “bottle” is used herein for ease of reference, and by way of illustration and not of limitation, as a container type in which a fluid (including fluid medication) may be contained.

A multi-dose bottle of fluid medication is typically marketed with a rubber membrane covering at least a portion of an opening at the top of the bottle, and the rubber membrane typically has a dimple in the center where it is intended for the rubber membrane to be penetrated for withdrawing the fluid. Conventionally, a syringe is used to withdraw some amount of fluid from the multi-dose bottle. In the prior art (prior to the invention of the syringe adapter disclosed in the related applications), this is done by attaching a needle to a tip of the syringe, inserting this needle into the multi-dose container through the rubber membrane (i.e., by piercing the dimple with the needle), and then withdrawing a plunger of the syringe until an appropriate amount of fluid is pulled into the syringe body (referred to equivalently herein as the syringe “barrel”), such that the eye of the needle serves as an entry point for the fluid to be drawn from the container into the syringe barrel. In the prior art, once the needle is removed from the multi-dose container, the needle can then be used for injecting at least some portion of the withdrawn fluid into a recipient. (The related applications describe how this withdrawal process is improved when using an embodiment of the syringe adapter, as disclosed therein, instead of using a needle.) Commonly, the recipient is an animal, such as a human being or a livestock animal; accordingly, discussions herein refer primarily to fluids that comprise medication intended for use with animals, by way of illustration but not of limitation.

One reason for marketing animal medication in multi-dose bottles is economic. The cost of the medication may be reduced, for example, by selling a larger quantity container and thereby reducing the relative cost of the packaging. Another reason for marketing animal medication in multi-dose bottles is that the dosage of many (if not all) medications is prescribed with regard to the animal’s body weight. Accordingly, the correct amount of medication to use on a particular animal can be calculated and then withdrawn from the multi-dose bottle, after which it may be injected into the animal, and the remaining medication is then available for subsequent use.

FIG. 1 shows an example of a prior art syringe 100, and illustrates how the hollow barrel 130 of syringe 100 is commonly marked with fill lines 110 that are provided for measuring the amount of fluid contained therein. When withdrawing fluid from a bottle prior to the invention of the syringe adapter disclosed in the related applications, a needle is placed over (or inside) the tip 140, and fluid enters through an opening or eye of the needle and into the syringe barrel 130. The syringe includes a retractable plunger, a terminal end of which is shown at 120. As will be obvious, fluid medication is withdrawn from the bottle into the barrel 130 by pulling the plunger 120 outwardly from the proximal end of the syringe 100 (although the extension, or movement, of the plunger outwardly from the syringe is not illustrated in FIG. 1). Commonly, a syringe as illustrated in FIG. 1 is constructed of plastic, making it relatively cheap to produce and to purchase.

A tab-shaped member 150 is also provided on syringe 100. When administering the medication from the barrel 130, a person’s index finger is placed on the tab-shaped member 150 at one side of barrel 130 and the person’s middle finger is placed on the tab-shaped member 150 at the opposing side of barrel 130, and the person’s thumb is then used to depress the terminal end of plunger 120 into the barrel in order to expel the medication from the barrel.

Figure 2:
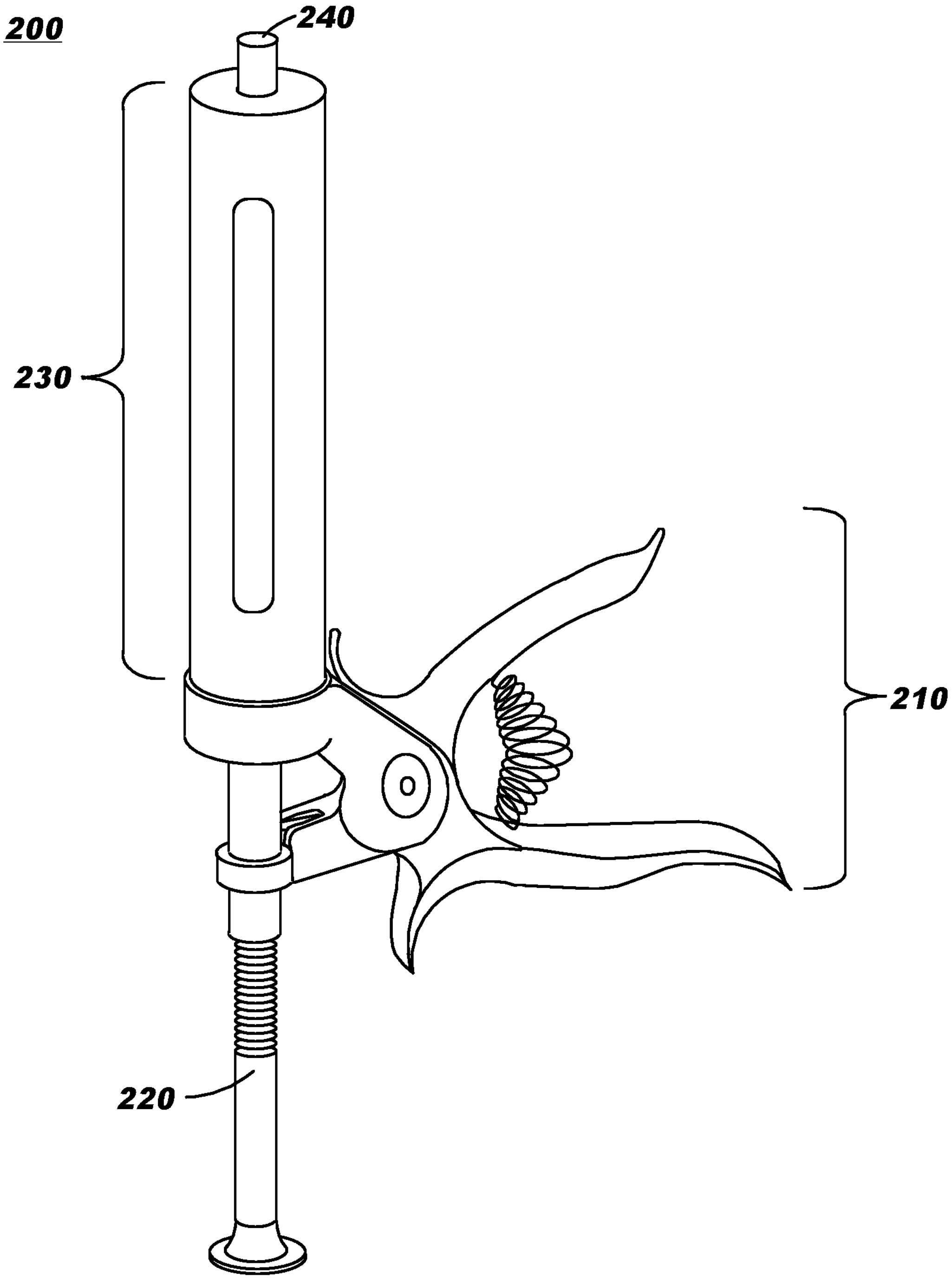
FIG. 2 (Prior Art)

As an alternative to the syringe 100 of FIG. 1, an example of a so-called “pistol-grip” syringe is illustrated in FIG. 2. When withdrawing fluid from a bottle prior to the invention of the syringe adapter disclosed in the related applications, a needle is attached to tip 240 and fluid enters through this needle, similar to the discussion presented above with reference to FIG. 1; fluid medication is drawn into a syringe of this type by pulling plunger 220 outwardly from the barrel 230. A tab-shaped member is not provided on a syringe of this type, as compressing or squeezing the handles 210 serves to expel medication from the barrel of a syringe having a pistol-grip configuration.

Figure 3:
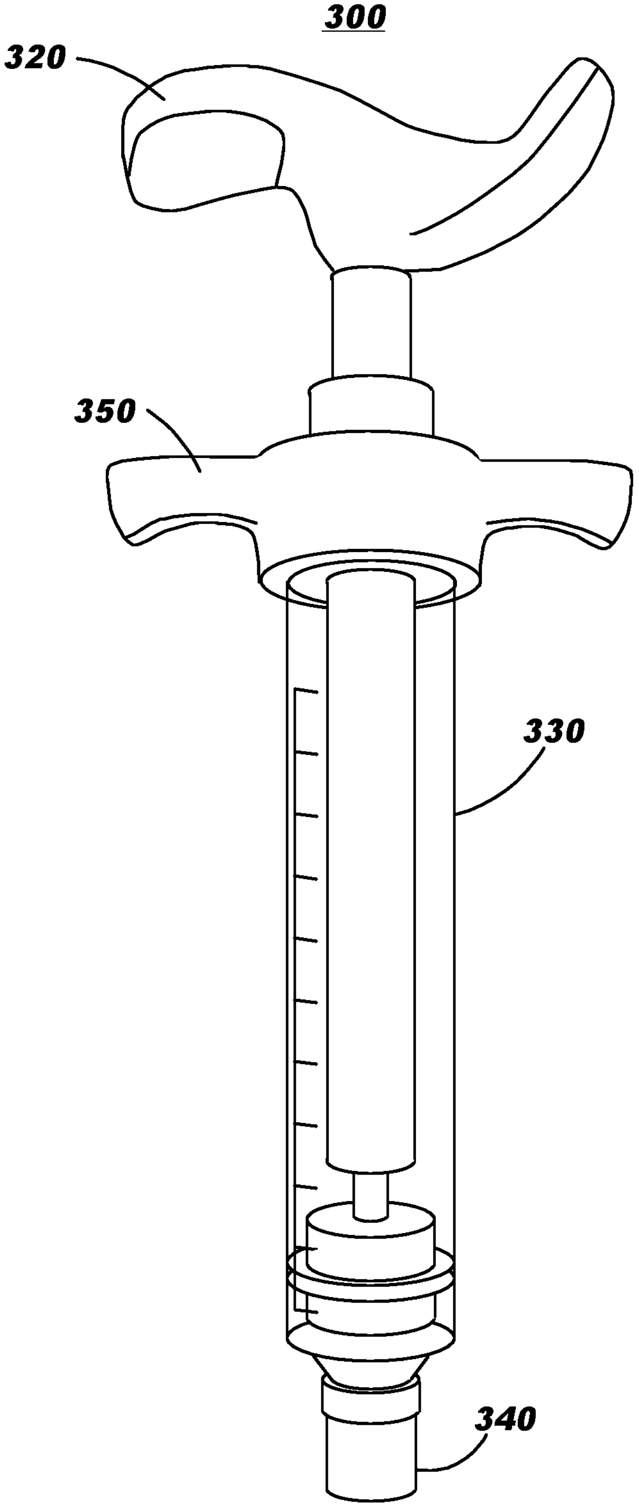
FIG. 3 (Prior Art)

FIG. 3 illustrates yet another prior art syringe 300, and is referred to herein as a “tab-handled” syringe. In this configuration, the syringe has a tabbed member 350 near the proximal end of barrel 330, and includes a handle-style tabbed member 320 affixed to the terminal end of the plunger. The tabbed member 350 is used in a similar manner to tab-shaped member 150 of FIG. 1, whereby a person places fingers on the tabbed member 350 on opposing sides of barrel 330; the person then presses down on tabbed member 320 using the person’s palm to depress the terminal end of the plunger into the barrel in order to expel the medication from the barrel. When withdrawing fluid from a bottle prior to the invention of the syringe adapter disclosed in the related applications, a needle is attached to tip 340 and fluid enters through this needle, similar to the discussion presented above with reference to FIG. 1; fluid medication is drawn into a syringe of this type by pulling handle 320 to thereby draw the attached plunger outwardly from the barrel 330. As compared to tab-shaped member 150 and plunger end 120 of FIG. 1, the tabbed members 320, 350 of FIG. 3 typically provide improved comfort for the person using the tab-handled syringe.

The tips 240, 340 may be generally on the order of ⅜ to 7/16 inch in diameter and generally of similar height (and similarly, tip 140), and are generally constructed of metal. An interior area of this tip is intended for securably attaching a needle and is generally threaded for at least a portion thereof. A height of this threaded area is believed to be generally on the order of ⅛ inch to ¼ inch (and it is believed that a height of 5.4 millimeters, or approximately 0.2125 inches, is used for syringe tip threads that conform to ISO 80369-7:2016, which is further discussed below). While not illustrated in detail on tips 240, 340 of FIGS. 2 and 3, the syringe tip also typically includes a protrusion (see, for example, the illustration at reference number 741 of FIG. 8C) that is centered within the exterior wall of the tip and that provides the opening through which a substance enters into the syringe barrel. (Notably, tips 140, 240, 340 are not designed for inserting through the rubber membrane of a medicine bottle.)

Syringes 200, 300 are often constructed, at least in part, of metal. Glass or plastic might be used for the syringe barrel. A metal commonly used for syringes, by way of example, is stainless steel; another example is aluminum.

Embodiments of the present invention are depicted (for example, in FIG. 7) as enabling attachment of a syringe having a form similar to the shape shown at 100 in FIG. 1 for ease of illustration, although in actual operation, it may be preferable to use a pistol-grip syringe 200 or tab-handled syringe 300 of the form illustrated in FIGS. 2-3, respectively. It is not material to an understanding of the present invention, for example, as to whether the syringe has handles 210 as shown in FIG. 2 or tabbed members 320, 350 as shown in FIG. 3, or has the simpler shape shown in FIG. 1. Accordingly, the form of syringe illustrated at reference number 700 in FIG. 7 et seq. is for ease of illustration only, and should not be construed as limiting the particular type of syringe that may be used advantageously with an embodiment of the disclosed container adapter. (Reference number 700 is used in FIG. 7 et seq., rather than reference number 100, so as to clarify that the syringe shown in those figures is not necessarily identical to syringe 100 of FIG. 1.)

As noted earlier, embodiments of the present invention provide a container adapter that attaches to a container, the container adapter directed toward securely holding a syringe adapter (the syringe adapter configured for providing a fluid path between a container and a syringe) and thereby also securing the syringe adapter to the container, the container adapter thereby providing an attachment point for a syringe that secures the syringe to a bottle (at least) while fluid is being withdrawn from the bottle and into the syringe barrel. The related applications describe, in detail, how the proximal end of a syringe adapter may be attached to the distal end of a syringe, or more particularly, to a syringe tip on the distal end of the syringe. It is noted that a conventional prior art syringe is marketed with the expectation that a needle will be attached to this distal end of a syringe, and accordingly, the distal end syringe tips 140, 240, 340 typically conform to the standard size of the proximal end of a needle. The related applications describe how the proximal end of an embodiment of the syringe adapter disclosed therein is preferably configured in a similar manner to the proximal end of a needle (thereby enabling the syringe adapter to be attached to a commercially-available syringe).

More particularly, the related applications describe the proximal end of some embodiments of the syringe adapter disclosed therein as having a flanged area that extends laterally therefrom, where the flanged area is designed (in these embodiments) to securably attach to a corresponding receiving area on the distal end of a syringe. This approach for making a securable attachment between two parts is commonly referred to as a Luer-type lock approach. Luer-type locks and Luer-type slips are known approaches for making leak-free connections on fluid fittings, and are described in International Standards 594-1:1986 and ISO 594-2:1998(E) and their replacement ISO 80369-7:2016, which are directed toward conical fittings for health-care applications. As is readily understood, a Luer-type lock relies upon a threaded attachment of what are commonly denoted as “male” and “female” parts, which may be achieved by placing tabs as lateral extensions on one part, these tabs designed to rotatably descend within corresponding threads of the other part. The threads are designed as a so-called “double start” or double helix configuration, as described for the internal threads of a Luer-type lock hub in the above-noted International Standards. The related applications disclosed embodiments that use this type of flanged area, also referred to as tabs, to thereby make a secure connection—by a Luer-type lock approach—between the syringe adapter and a syringe.

As an alternative to connecting a syringe to a syringe adapter using a Luer-type lock, the related applications also describe other embodiments of the syringe adapter disclosed therein as relying on a friction-based connection. Prior to invention of the syringe adapter disclosed in the related applications, this type of connection relied on friction to attach a needle to a syringe tip, and is known as a Luer-type slip connection. The related applications include embodiments that use a friction-based, or Luer-type slip, connection whereby the proximal end of those embodiments of the syringe adapter is placed over an exterior of the distal end (e.g., tip 140 of FIG. 1) of a syringe.

While discussions herein primarily refer to a syringe adapter embodiment having a proximal end configured with tabs and thus adapted for making a Luer-type lock connection, and a syringe having a syringe tip that accommodates a Luer-type lock connection, this is by way of illustration but not of limitation: in view of teachings herein, it can be seen that the disclosed container adapter may alternatively be used in a Luer-type slip connection between syringe and syringe adapter.

The related applications describe removably attaching a syringe adapter to a syringe, then withdrawing fluid from a bottle through an opening in the distal end of the syringe adapter, through a hollow chamber of the syringe adapter and then through a proximal end opening of the syringe adapter as it meets with an opening in the syringe tip, and then into the syringe barrel. The related applications also describe that in some embodiments, the syringe adapter is configured for affixing a needle onto the in-place syringe adapter for administering the medication from the syringe barrel, while in other embodiments, the syringe adapter is configured to be removed from the syringe after the withdrawing of fluid and then replaced with a needle in order to administer medication from the syringe barrel. Preferred embodiments of the container adapter of the present invention are configured for use with a syringe adapter embodiment of the latter form.

The container adapter disclosed herein provides a novel, non-obvious mechanism for securing the syringe adapter to the container that then facilitates attachment of the syringe, and also facilitates novel and non-obvious methods of use, as will now described in detail with reference to several embodiments thereof.

FIGS. 4-8 illustrate a first embodiment of the container adapter disclosed herein.

Figure 4:
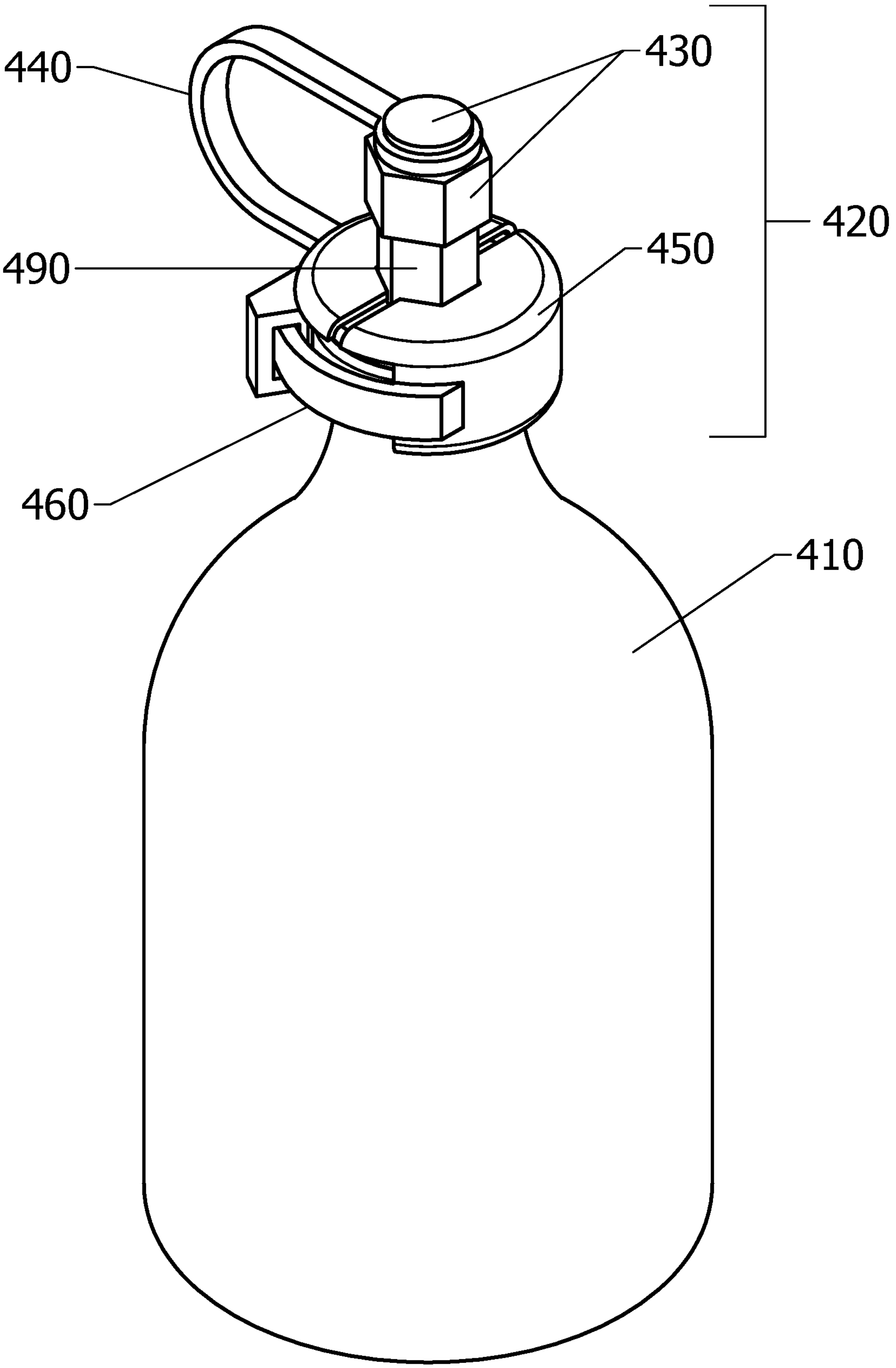
FIG. 4 depicts an as-assembled view of a container with container adapter fitted thereupon, according to a first embodiment of the present invention, and is shown as a perspective view.

FIG. 4 depicts an as-assembled view of a container/bottle 410 with a container adapter 420 fitted thereupon, the container adapter 420 securing therein a syringe adapter 490 (as shown in further detail in FIGS. 5-8). A cap 430 is shown as being closed, thus preventing fluid in bottle 410 from leaking or spilling out. A lanyard 440 is attached to the cap 430. In this embodiment, a component 450 is attached to the other end of lanyard 440. Component 450 is formed so as to open, allowing syringe adapter 490 to be placed within an interior of component 450, and a strap 460 is placed so as to securely hold component 450 in a closed position around the syringe adapter 490, as will now be discussed in more detail with reference to FIGS. 5 and 6.

Figure 5A:
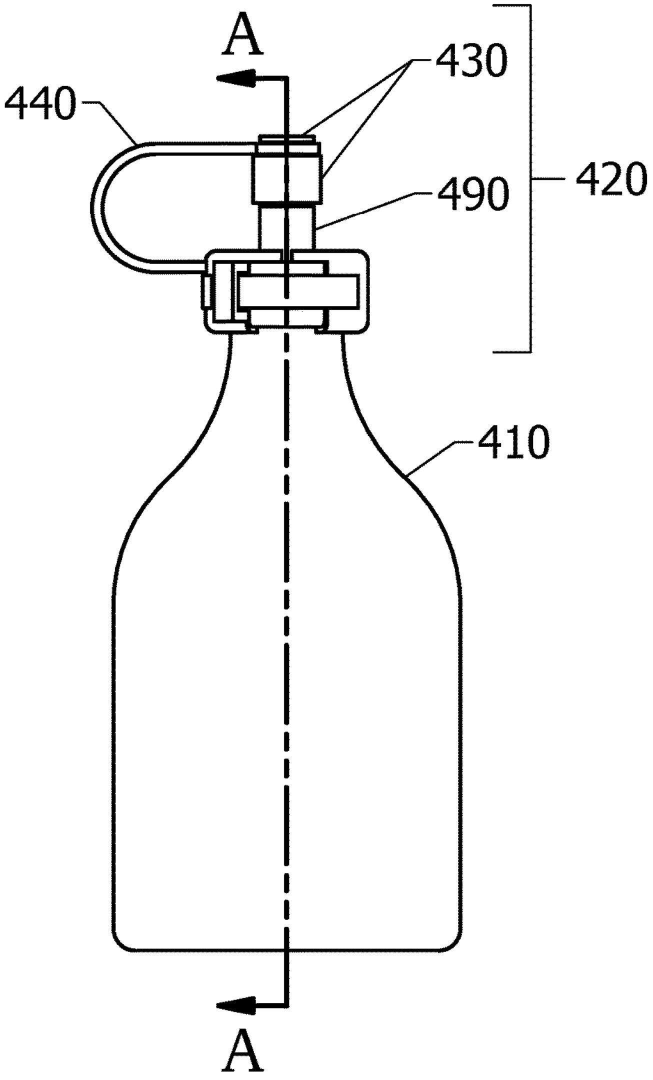
FIG. 5 (comprising FIGS. 5A-5C) illustrates a side view, a cross-sectional view along an imaginary line depicted using dashes in FIG. 5A, and a close-up view of a portion of the cross-sectional view, respectively, according to the first embodiment.
Figure 5B:
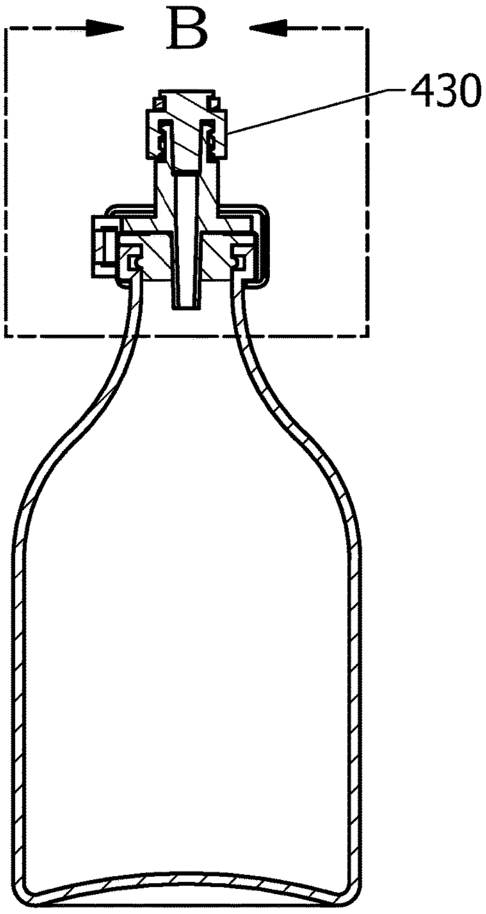
Figure 5C:
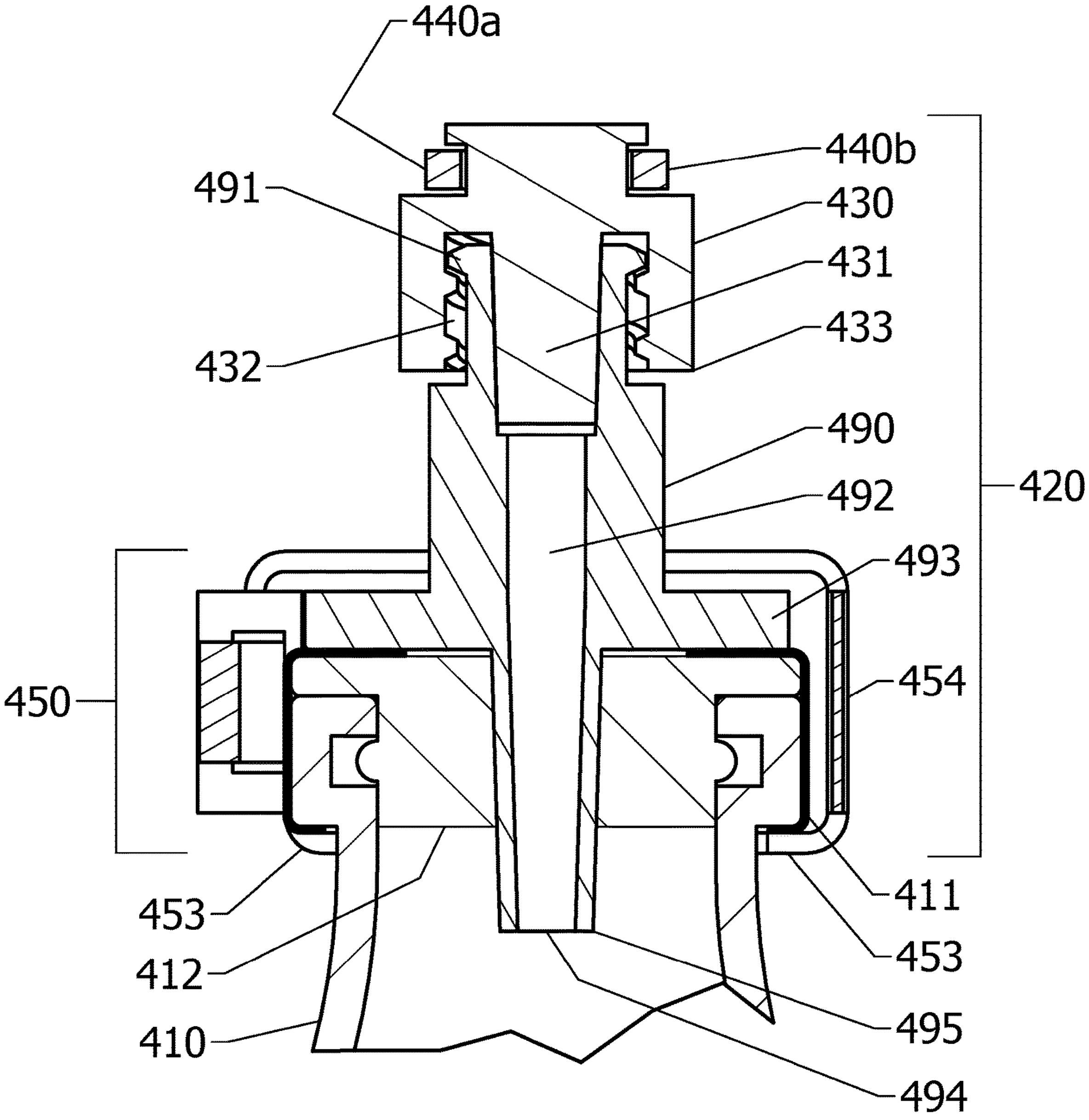

FIG. 5A illustrates a side view of this first embodiment, showing container adapter 420 placed upon bottle 410. FIG. 5B provides a cross-sectional view along an imaginary line that is denoted as "A" and depicted using dashes in FIG. 5A. FIG. 5C provides a close-up view of a portion of the cross-sectional view of FIG. 5B, this portion denoted as "B" in FIG. 5B, and for ease of reference, discussions will now refer to the close-up view in FIG. 5C.

FIG. 5C illustrates how cap 430 is placed on (i.e., removably connected to) a syringe adapter 490, thus closing off entry and exit into bottle 410. Reference numbers 440*a*, 440*b* represent portions of a ring-shaped end of lanyard 440 as it surrounds a top portion of cap 430. Preferably, portions of cap 430 are configured to mimic portions of a syringe tip from a conventional syringe. More particularly, cap 430 is depicted as having a protruding tip 431 and a threaded inner attachment area 432. (Notably, tip 431 does not have a through-hole, as distinguished from a conventional syringe tip.) In the approach depicted in FIG. 5C, the tip 431 protrudes somewhat from an edge 433 of cap 430 and into the hollow chamber 492 of the syringe adapter 490. (Note that while chamber 492 is illustrated as having a generally cylindrical shape at one end and a generally conical or tapered shape at the other end, and that while syringe adapter 490 is illustrated as having particular dimensions, this is by way of illustration but not of limitation, and an embodiment of the disclosed container adapter may be suitably configured to accommodate varying outer shapes and dimensions of syringe adapters without deviating from the scope of the present invention.)

Cap 430 is preferably configured with a multi-sided exterior (shown in FIGS. 4-8 as being hexagonal, by way of illustration but not of limitation). This multi-sided exterior shape enables a user to twist and/or grip the cap with relative ease (for example, when attaching and removing the cap). Accordingly, a secure and leak-free Luer-lock type connection between cap 430 and syringe adapter 490 may be made by rotating/twisting cap 430 (and/or syringe adapter 490) until a flanged area 491 (which may also be referred to as tabs, as noted earlier, a "flanged area" as referred to herein preferably comprising a pair of tabs placed generally opposite one another) that extends laterally from a proximal end of syringe adapter 490 (i.e., the end where reference number 491 is generally pointing) moves within internal threaded area 432 of cap 430 until flanged area 491 locks into place within threaded area 432. Notably, this is the same approach for making a leak-free connection that will preferably be used when connecting a syringe to the syringe adapter 490 (as will be discussed in further detail with reference to FIGS. 7 and 8). As noted earlier, a conventional height for the internal threaded portion of a tip of a pistol-grip or tab-handled syringe is believed to be approximately ⅛ inch to ¼ inch in length and a standardized height thereof is believed to be 5.4 millimeters to conform with the above-cited International Standards. Accordingly, threaded area 432 of cap 430 preferably has a similar height so as to accommodate flanged area 491 on the proximal end of syringe adapter 490 (where a height of flanged area 491, as described in the related applications, is preferably on the order of at least 1⁄16 to ⅛ inch in height in view of the height of the syringe tip threads).

It should be noted that while a Luer-type connection is designed to be "leak-free", references herein to such characterization are not meant to imply that the connection provided by an embodiment of the disclosed container adapter necessarily prevents fluid from leaking from a container under all circumstances. Thus, such references may be interpreted more generally as leak resistant.

Figure 6:
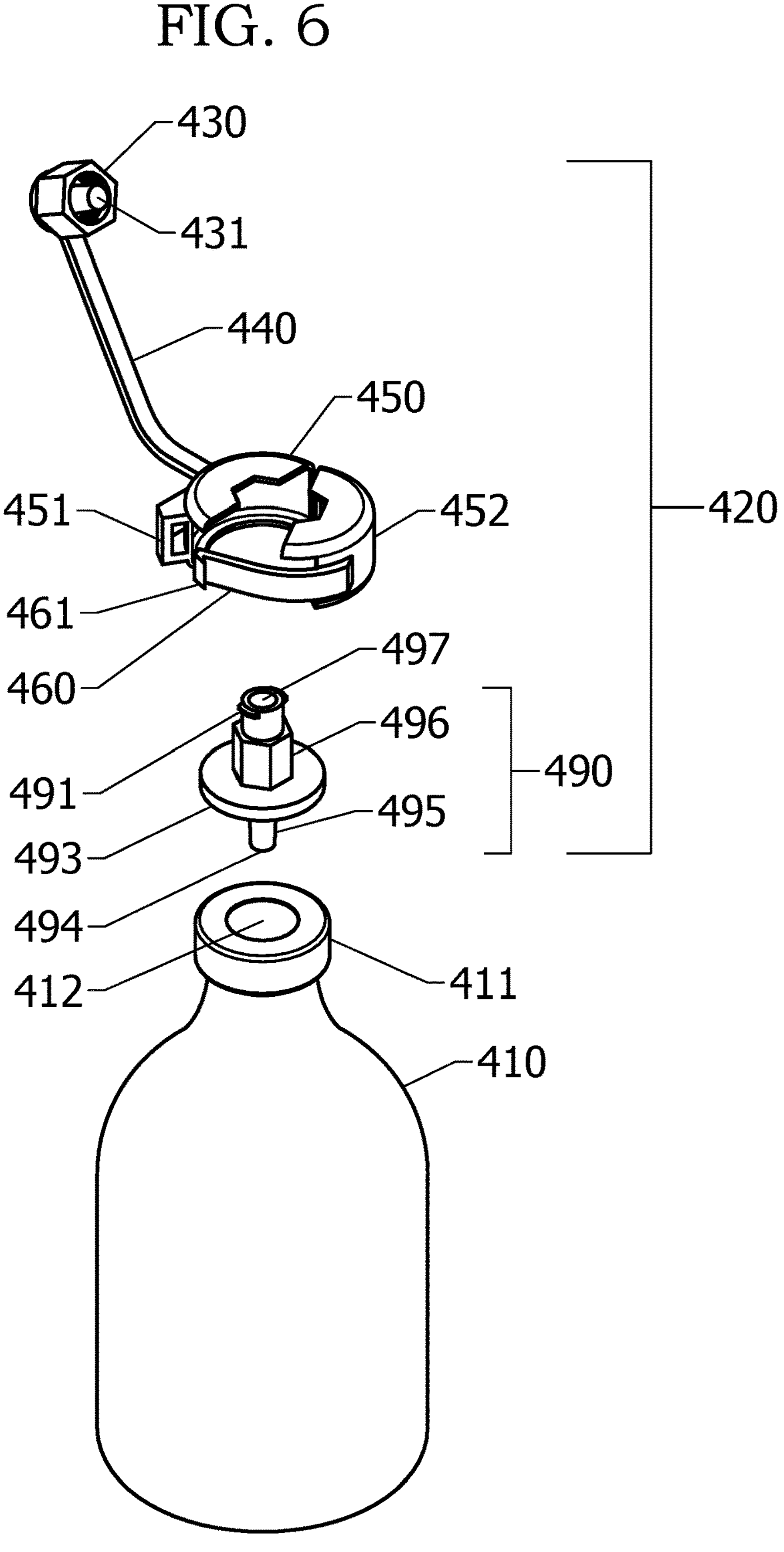
FIG. 6 illustrates an exploded view showing individual components of the assembly depicted in FIG. 4.

Reference number 411 depicts a conventional collar on bottle 410, and FIG. 5C illustrates how component 450 is designed to surround this collar 411 to thereby secure the container adapter 420 (and thus the syringe adapter 490) to the bottle 410. An inner diameter of component 450, when a sidewall 452 thereof is closed, is preferably only slightly larger than the diameter of an exterior of collar 411. (Reference number 452 is shown in FIG. 6.) In this manner, component 450 will fit snugly around collar 411, and will be less likely to slip or spin. Similarly, a height of sidewall 452 is preferably only slightly taller than a sum of the height of collar 411 and the height of extension 493 of syringe adapter 490. In addition to surrounding the top and outer edges of collar 411, FIG. 5C illustrates that component 450 is further configured with a lip 453 at its lower edge (i.e., at the lower edge of sidewall 452) that hooks underneath collar 411. Reference number 454 depicts an area where sidewall 452 flexes as it is opened or closed.

FIG. 5C also illustrates how container adapter 420 is configured to encapsulate an extension 493 of syringe adapter 490, extension 493 being configured in this example as a radial extension. (Note that while the extension 493 is illustrated as being round at its perimeter, and the exterior dimension thereof is shown as fully extending within the bounds of the interior diameter of component 450, this is by way of illustration but not of limitation.) A conventional bottle 410 typically includes a rubber membrane covering at least a portion of an opening at the top of the bottle and the rubber membrane typically has a dimple (e.g., a small indentation) in the center where it is intended for the rubber membrane to be penetrated, as noted earlier, and this membrane is illustrated at reference number 412 in FIG. 5C. Commonly, collar 411 is made from metal and is used to hold membrane 412 over an opening in the neck of the bottle 410. A distal end 495 of syringe adapter 490 penetrates and extends through this membrane 412 (and is held in this position by container adapter 420), thus allowing fluid within bottle 410 to contact, and enter through, an opening 494 in the distal end 495 of the syringe adapter (this opening 494 illustrated as being formed by the sidewall of syringe adapter 490 and located at the terminal end of distal end 495 and being generally blunt and frusto-conical in shape, as contrasted to the sharp end of a needle).

Figure 7:
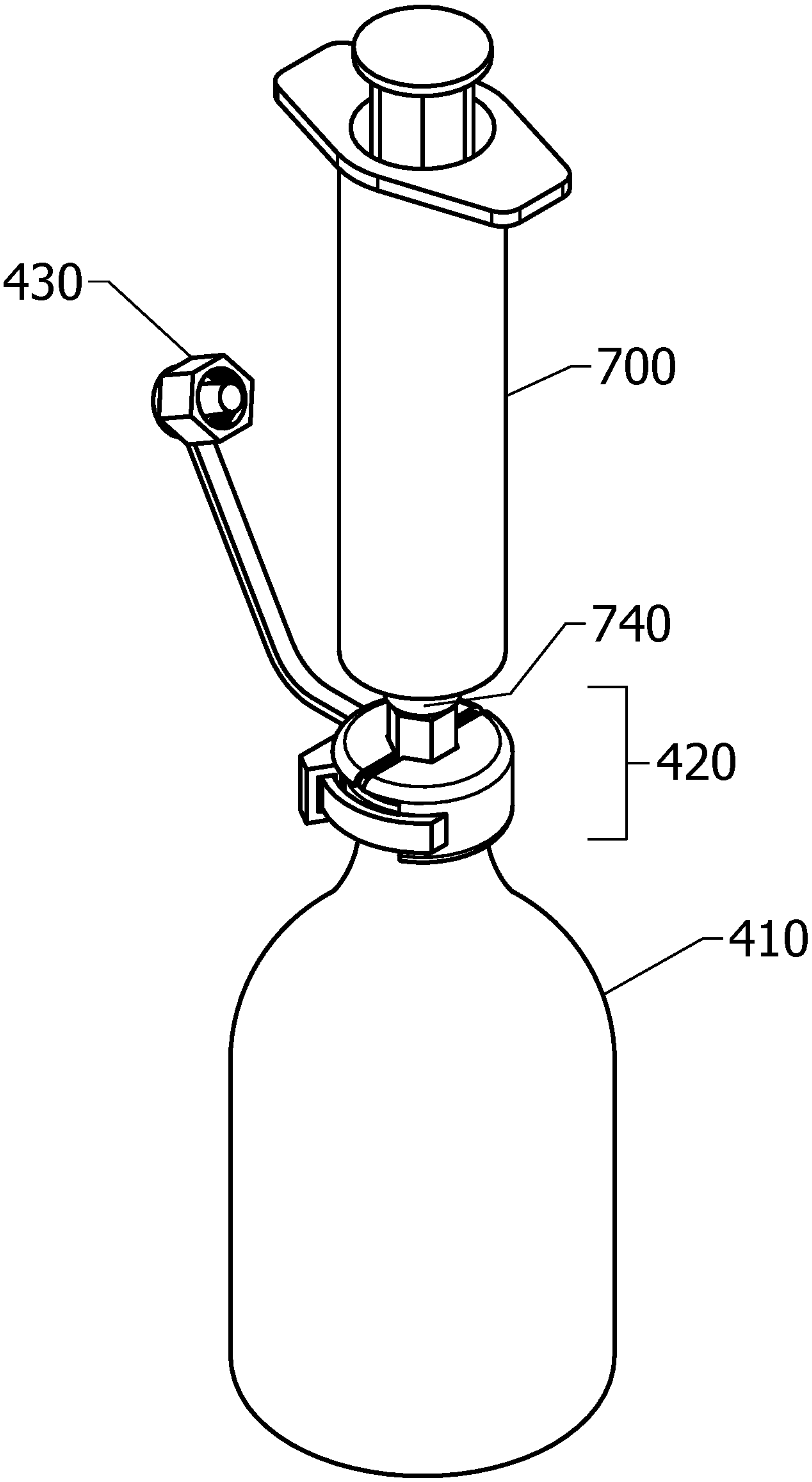
FIG. 7 illustrates an as-assembled perspective view of the container with container adapter fitted thereupon from FIG. 4, now illustrating how a syringe may be attached thereto.

FIG. 6 illustrates an exploded view showing individual components of the assembly depicted in FIG. 4. A conventional bottle 410 is illustrated with its collar 411 and membrane 412. A syringe adapter 490 is illustrated, showing its flanged area 491, proximal end opening 497, extension 493, distal end 495, and the location therein of opening 494. Component 450 is shown as separating at the top, preferably along a center thereof, and is designed to flex open. As shown in FIG. 6, one side of sidewall 452 of component 450 is designed to open during this flexing, while a side opposite thereto is formed as a continuous piece that flexes or bends (see 454 of FIG. 5C) but does not open. By way of illustration but not of limitation, an opening or cut-out in the center area of the top of component 450 forms (when closed) a hexagonal shape, as can be seen in FIGS. 6 and 7. This hexagonal cut-out shape accommodates a corresponding hexagonal exterior shape of a portion 496 of syringe adapter 490, holding the syringe adapter in place so that it does not spin. Using a hexagonal (or more generally, multi-sided) exterior shape for portion 496 assists a person in easily grasping the syringe adapter 490—for example, when connecting syringe adapter 490 within the inner threaded area 432 of cap 430 and/or (as shown in FIGS. 7 and 8) the inner threaded area 732 of a syringe tip 740. (As will be obvious in view of teachings herein, if a syringe adapter is used that has a different shape for this exterior portion—for example, being cylindrical in shape or having a multi-sided exterior with a different number of sides—then the cut-out in the center area of the top of component 450 is preferably configured to match that exterior shape. Furthermore, while FIG. 6 depicts syringe adapter 490 as being completely separable from component 450, it should be understood in view of teachings herein that this is by way of illustration and not of limitation. As an alternative, syringe adapter 490 may be molded to, or otherwise affixed to, the top of component 450—for example, by being attached to one of the sides of the top of component 450 in the area where the cut-out in the center is depicted—without deviating from the scope of the present invention.)

FIG. 6 also illustrates how strap 460 is preferably designed to extend from an area on one end of sidewall 452, while an opposite end of sidewall 452 includes an extension 451 having an opening into which the loose end 461 of strap 460 is to be inserted. Strap 460 may be manufactured to curve (at least somewhat) from its attachment point on sidewall 452 toward its loose end 461. Preferably, strap 460 and extension 451 are configured similarly to a well-known "zip tie", such that once the component 450 is in place surrounding the syringe adapter 490 and the bottle collar 411, the loose end 461 may be pulled through the opening in extension 451 and tightened. Loose end 461 is preferably configured with at least one protrusion that prevents strap 460 from being backed out of the opening in extension 451. As a result, the component 450 of container adapter 420 enables the syringe adapter 490 to be securably attached to the bottle 410. See FIG. 7, where this attachment is illustrated. The attachment is preferably used as a permanent attachment, although if strap 460 is constructed from a material that can be severed, it would be possible to detach the container adapter 420 from bottle 410 if desired.

FIG. 6 also illustrates cap 430 and its protrusion 431, the cap being attached to lanyard 440 which in turn is attached to component 450. Preferably, lanyard 440 is of sufficient length as to allow cap 430 to not interfere with other portions of the assembly when the cap is opened (as illustrated in FIG. 7).

As illustrated in FIG. 6, the container adapter 420 of this first embodiment is designed such that component 450 is assembled over a syringe adapter 490 and collar 411 prior to locking the component 450 closed with strap 460 and extension 451. In one approach, this assembly is performed in a manufacturing or distribution step, prior to delivery of the bottle to a user. In another approach, this assembly is performed by a user, thus enabling the user to attach the container adapter—including the syringe adapter it secures—to a suitably-sized bottle. In this latter approach, the container adapter and its syringe adapter may be packaged together so that the user receives all needed components; as an alternative, components of the container adapter may be provided separately, such that (for example) a user receives component 450 with lanyard 440 and cap 430 attached thereto, and then provides his or her own syringe adapter during the assembly process. (The term "user", as used herein, should be construed as including end users who extract fluid for administering with a syringe and also other humans such as veterinarians who may prepare containers of fluid medication for other users.)

The related applications describe various materials from which a syringe adapter may be constructed, noting that choices include plastics (or composites) and metal. Similarly, other elements of container adapter 420 (including the cap 430, lanyard 440, component 450, and strap 460) may be constructed from a plastic or a composite, or from another material such as stainless steel, aluminum, or another metal (or a combination thereof), without deviating from the scope of the present invention. (It will be readily understood that constructing the container adapter from a material such as plastic advantageously allows it to be recyclable, in addition to being easily disposable.)

FIG. 7 illustrates an as-assembled perspective view of bottle 410 with container adapter 420 fitted thereupon from FIG. 4, now illustrating how a syringe 700 may be attached thereto. Syringe 700, as noted earlier, is shown (for ease of illustration) as having a form similar to the shape of syringe 100 of FIG. 1, and it should be understood that syringe 700 illustrates merely one example shape. As noted earlier, embodiments of the container adapter are described (and illustrated) herein primarily with reference to containing (i.e., securing) a syringe adapter having a proximal end configured with tabs and thus adapted for making a Luer-type lock connection with a syringe tip that accommodates such connection, and accordingly, the syringe tip shown at reference number 740 of FIG. 7 is described as having a configuration with an internal threaded area (as further shown in FIG. 8).

FIG. 7 shows that cap 430 is now opened, and the tip 740 at the distal end of syringe 700 takes it place. Accordingly, a secure connection (referred to equivalently herein as, inter alia, a secure attachment or a leak-free connection) is made between tip 740 and the proximal end of syringe adapter 490 (this proximal end being contained inside tip 740 and thus not being visible in FIG. 7). FIG. 8 illustrates this secure connection in further detail.

Figure 8A:
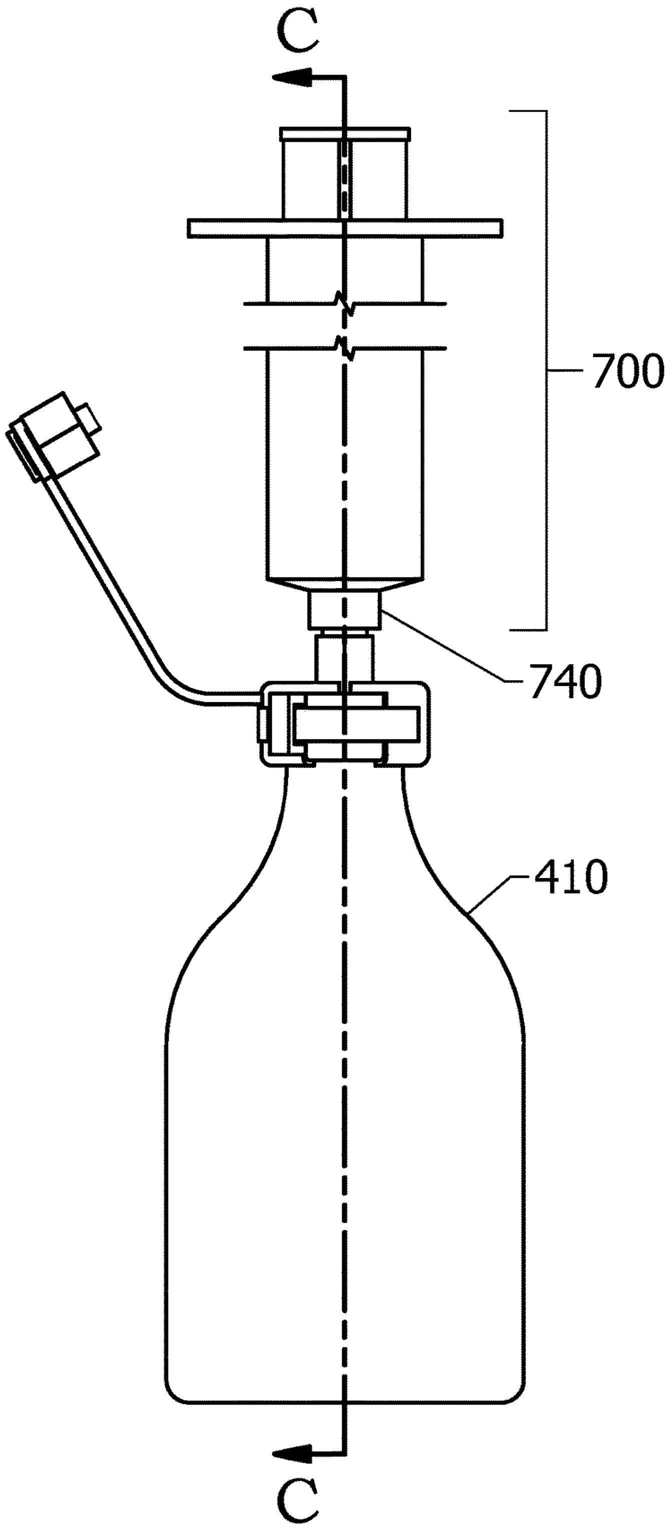
FIG. 8 (comprising FIGS. 8A-8C) depicts further details of the assembly illustrated in FIG. 7, including a side view, a cross-sectional view along an imaginary line depicted using dashes in FIG. 8A, and a close-up view of a portion of the cross-sectional view, respectively.
Figure 8B:
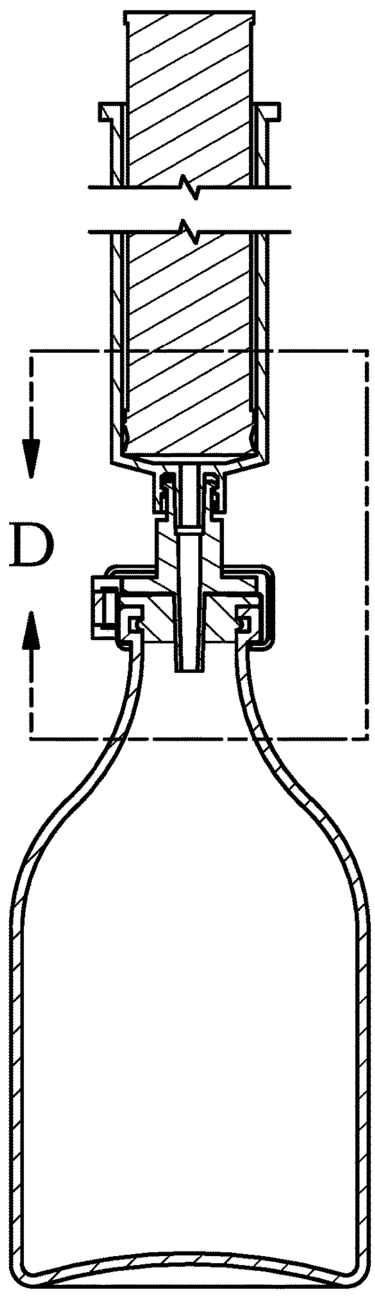
Figure 8C:
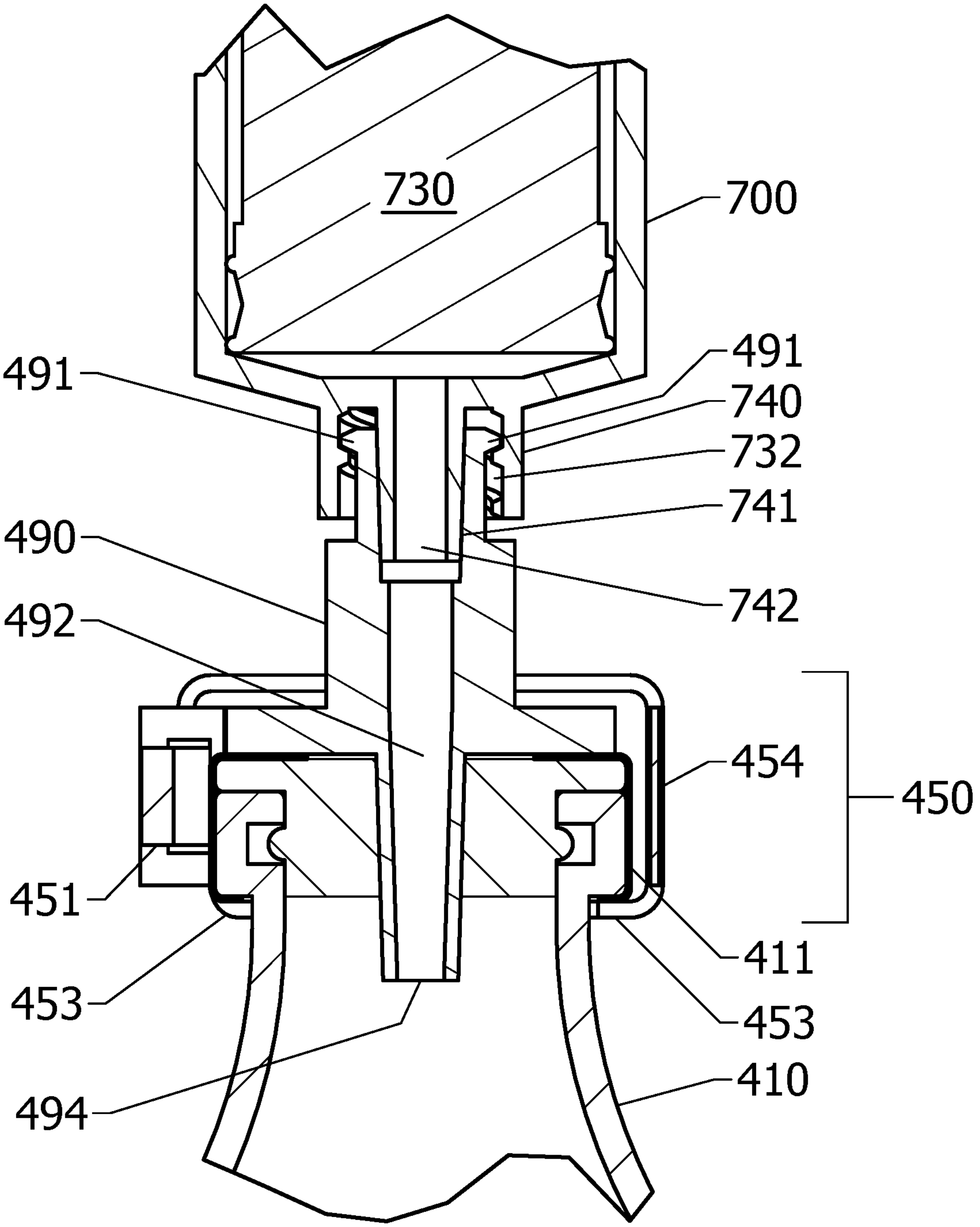

FIG. 8A illustrates a side view of the assembly shown in FIG. 7, with syringe 700 attached to bottle 410. FIG. 8B provides a cross-sectional view along an imaginary line that is denoted as "C" and depicted using dashes in FIG. 8A. FIG. 8C close-up provides a close-up view of a portion of the cross-sectional view of FIG. 8B, this portion denoted as "D" in FIG. 8B, and for ease of reference, discussions will now refer to the close-up view in FIG. 8C.

FIG. 8C shows the component 450 of the container adapter surrounding collar 411 to thereby secure the container adapter 420 to the bottle 410 while encapsulating syringe adapter 490, as has been discussed above with reference to FIG. 5C. FIG. 8C differs from FIG. 5C, however, in that the cap 430 is now opened and replaced with syringe 700 as noted above with reference to FIG. 7. FIG. 8C shows how syringe 700 is securably attached to syringe adapter 490, this attachment comprising inserting flanged area 491 into corresponding internal threads of threaded area 732 shown in the interior of syringe tip 740 and then twisting until flanged area 491 of the syringe adapter 490 locks into place within threaded area 732. As can be seen in FIG. 8C, the proximal end of syringe adapter 490 is preferably sized—as disclosed in one or more of the related applications—so as to slip over the protrusion 741 while at the same time, fitting within the threaded interior area 732 of syringe tip 740. (It is noted that the above-cited International Standard ISO 80369-7 states acceptable measurements for inner and outer diameters of male and female portions of components intended for a Luer-type lock connection. As discussed in one or more of the related applications, inner and outer diameters of the proximal end—i.e., the end where reference number 491 is generally pointing—are preferably designed for compatibility with such measurements to enable syringe adapter 490 to make a secure attachment to the internal threaded area 732 of a syringe tip 740 that is manufactured in conformance with such measurements.)

FIG. 8C depicts, in detail, how a fluid path exists for withdrawing fluid from bottle 410 through the opening 494 into the syringe adapter 490, then through the hollow chamber 492 of the syringe adapter 490, then through proximal end opening 497 (shown in FIG. 6) of the syringe adapter where it meets with an opening shown generally at 742 of protrusion 741, and finally into the barrel 730 of syringe 700. Because the disclosed container adapter securably connects all of the elements as illustrated in FIG. 8 (i.e., syringe, syringe adapter, and bottle), a user now has fewer things to hold and to manage during the withdrawal process and may therefore be less likely to experience problems while withdrawing fluid, as was noted earlier.

FIGS. 9-13 illustrate a second embodiment of the container adapter disclosed herein.

Figure 9:
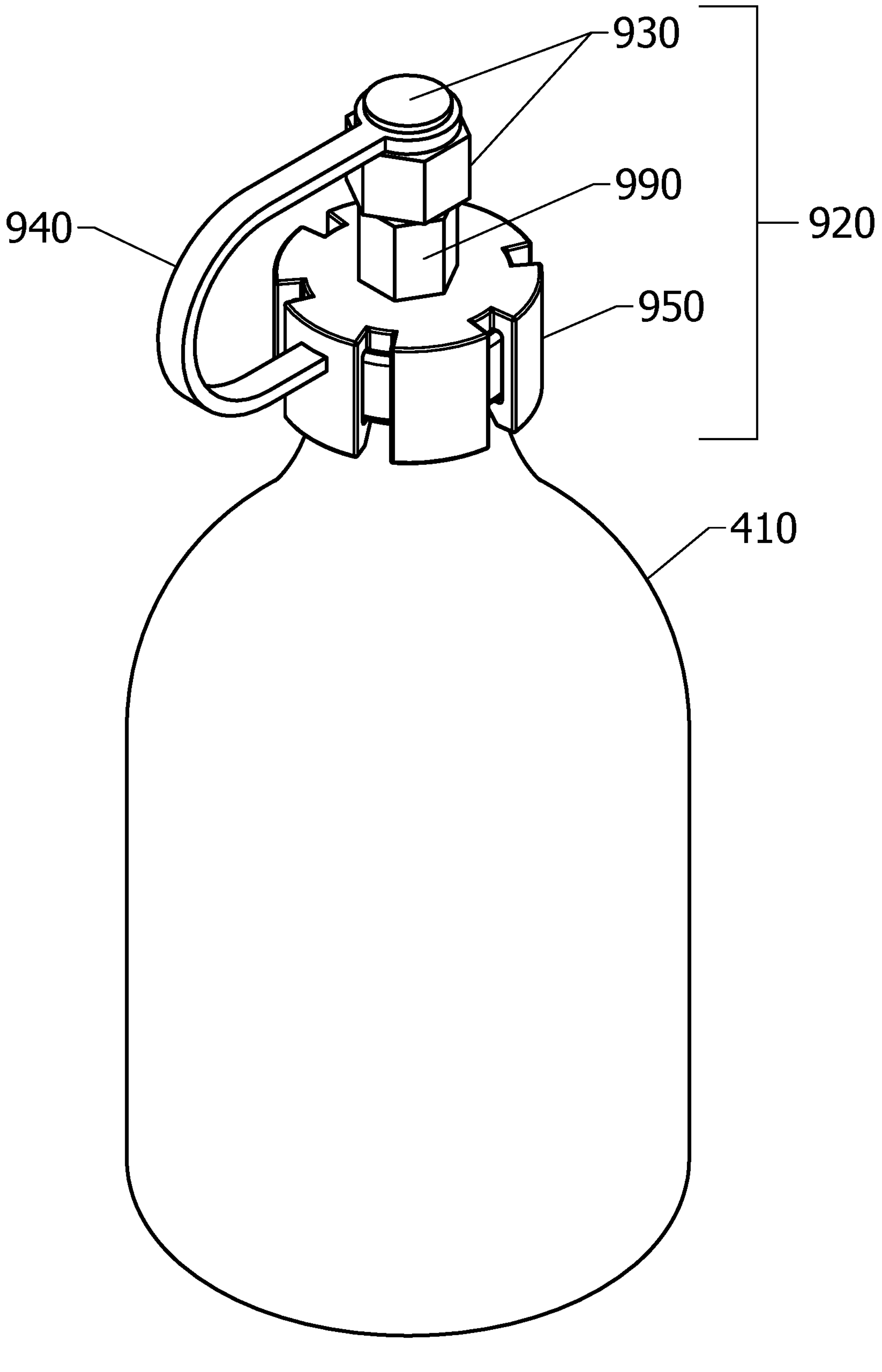
FIG. 9 depicts an as-assembled view of a container with container adapter fitted thereupon, according to a second embodiment of the present invention, and is shown as a perspective view.

FIG. 9 depicts an as-assembled view of a bottle 410 with a container adapter 920 fitted thereupon, the container adapter 920 securing therein a syringe adapter 990 (as shown in further detail in FIGS. 10-13). A cap 930 is shown as being closed, thus preventing fluid in bottle 410 from leaking or spilling out. A lanyard 940 is attached to the cap 930, and in this embodiment, a component 950 is attached to the other end of lanyard 940. In contrast to component 450 of FIG. 4, component 950 is not designed to open for insertion of a syringe adapter. Instead, a preferred embodiment of component 950 is manufactured so as to include a syringe adapter 990, as will now be discussed in more detail with reference to FIGS. 10 and 11. (Syringe adapter 990 may be similar, including identical, to syringe adapter 490. Cap 930 and lanyard 940 may also be similar, including identical, to cap 430 and lanyard 440.)

Figure 10A:
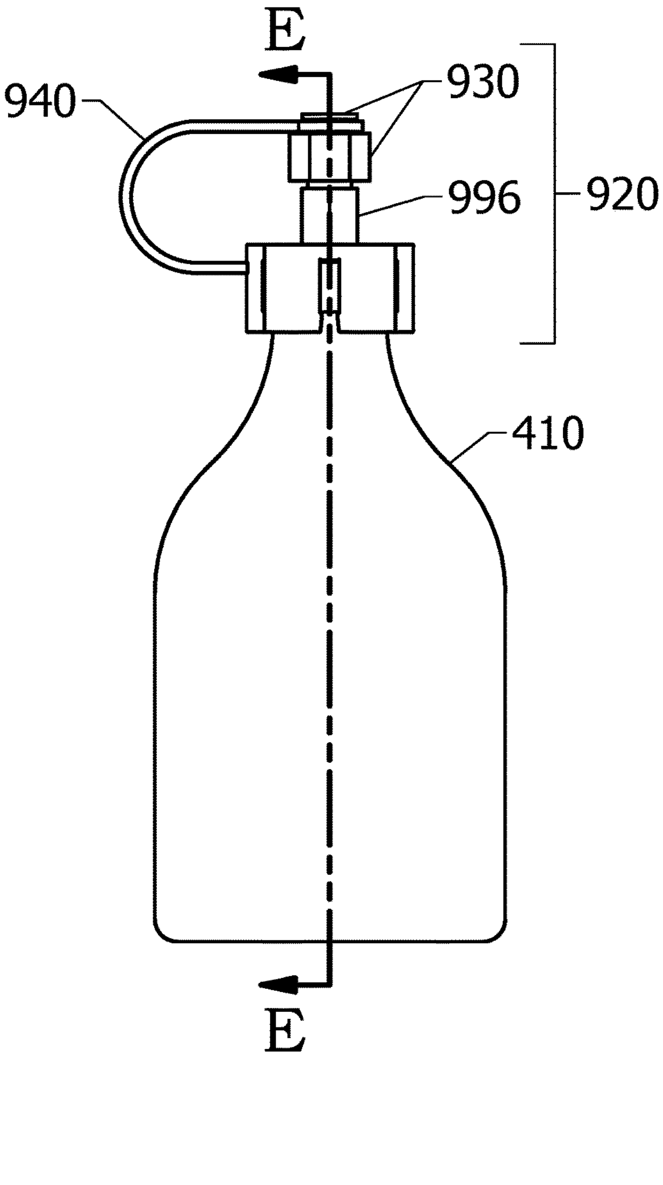
FIGS. 10A-10C illustrate a side view, a cross-sectional view along an imaginary line depicted using dashes in FIG. 10A, and a close-up view of a portion of the cross-sectional view, respectively, according to the second embodiment, and FIGS. 10D-10F provide a variation on the illustrations in FIGS. 10A-10C, respectively.
Figure 10B:
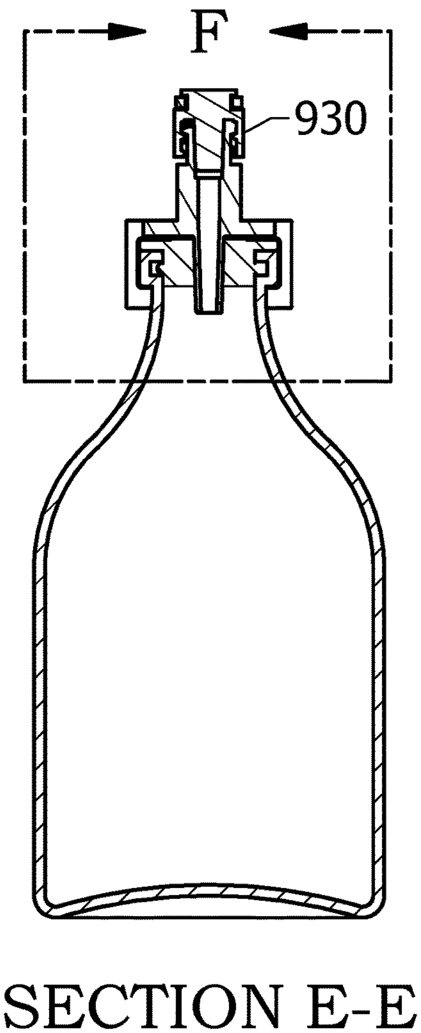
Figure 10C:
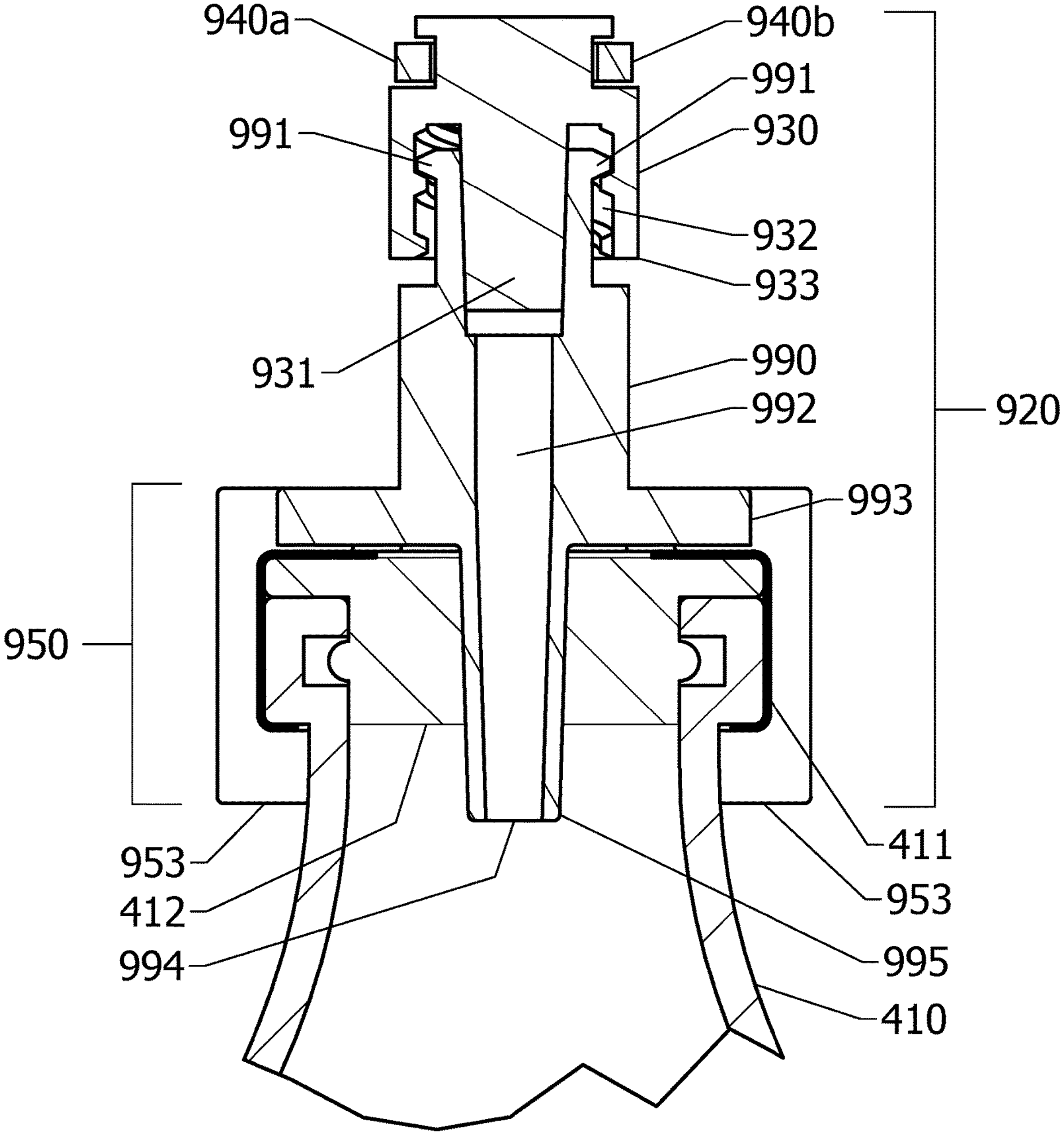

FIG. 10A illustrates a side view of this second embodiment, showing container adapter 920 placed upon bottle 410. FIG. 10B provides a cross-sectional view along an imaginary line that is denoted as "E" and depicted using dashes in FIG. 10A. FIG. 10C provides a close-up view of a portion of the cross-sectional view of FIG. 10B, this portion denoted as "F" in FIG. 10B, and for ease of reference, discussions will now refer to the close-up view in FIG. 10C.

FIG. 10C illustrates how cap 930 is placed on (i.e., removably connected to) a syringe adapter 990, thus closing off entry and exit into bottle 410. Reference numbers 940*a*, 940*b* represent portions of a ring-shaped end of lanyard 940 as its surrounds a top portion of cap 930. Preferably, portions of cap 930 are configured to mimic portions of a syringe tip from a conventional syringe. More particularly, cap 930 is depicted as having a protruding tip 931 and a threaded inner attachment area 932. (Notably, tip 931 does not have a through-hole, as distinguished from a conventional syringe tip.) In the approach depicted in FIG. 10C, the tip 931 protrudes somewhat from an edge 933 of cap 930 and into the hollow chamber 992 of the syringe adapter 990. (Note that while chamber 992 is illustrated as having a generally cylindrical shape at one end and a generally conical or tapered shape at the other end, and that while syringe adapter 990 is illustrated as having particular dimensions, this is by way of illustration but not of limitation, and an embodiment of the disclosed container adapter may be suitably configured to accommodate varying outer shapes and dimensions of syringe adapters without deviating from the scope of the present invention.)

Cap 930 is preferably configured with a multi-sided exterior (shown in FIGS. 9-13 as being hexagonal, by way of illustration but not of limitation). This multi-sided exterior shape enables a user to twist and/or grip the cap with relative ease. Accordingly, a secure and leak-free Luer-type lock connection between cap 930 and syringe adapter 990 may be made by rotating/twisting cap 930 (and/or syringe adapter 990) until a flanged area 991 extending laterally from a proximal end of syringe adapter 990 (i.e., the end where reference number 991 is generally pointing) moves within internal threaded area 932 of cap 930 until flanged area 991 locks into place within threaded area 932. Notably, this is the same approach for making a leak-free connection that will preferably be used when connecting a syringe to the syringe adapter 990 (as will be discussed in further detail with reference to FIGS. 12 and 13). As noted earlier, a conventional height for the internal threaded portion of a tip of a pistol-grip or tab-handled syringe is believed to be approximately ⅛ inch to ¼ inch in length and standardized height thereof is believed to be 5.4 millimeters to conform with the above-cited International Standards. Accordingly, threaded area 932 of cap 930 preferably has a similar height so as to accommodate flanged area 991 on the proximal end of syringe adapter 990 (where a height of flanged area 991, as described in the related applications, is preferably on the order of at least 1⁄16 to ⅛ inch in height in view of the height of the syringe tip threads).

Reference number 411 depicts a conventional collar on bottle 410, and FIG. 10C illustrates how component 950 is designed to surround this collar 411 to thereby secure the container adapter 920 (and thus the syringe adapter 990) to the bottle 410. In addition to surrounding the top and outer edges of collar 411, FIG. 10C illustrates that component 950 is further configured with a lip area 953 (discussed below with reference to sides 951) that hooks underneath collar 411. An inner diameter of component 950 is preferably only slightly larger than the diameter of an exterior of collar 411. In this manner, component 950 will fit snugly around collar 411, and will be less likely to slip or spin. Similarly, a height of the outside of sides 951 (see FIGS. 11 and 13C) is tall enough to enable a secure fit around collar 411, as shown in FIG. 13C.

FIG. 10C also illustrates how container adapter 920 is configured to encapsulate an extension 993 of syringe adapter 990, extension 993 being configured in this example as a radial extension. (Note that while the extension 993 is illustrated as being round at its perimeter, and the exterior dimension thereof is shown as fully extending within the bounds of the interior diameter of component 950, this is by way of illustration but not of limitation.) A rubber membrane covering at least a portion of an opening at the top of the bottle 410, and typically including a dimple as noted earlier, is illustrated at reference number 412 in FIG. 10C. A distal end 995 of syringe adapter 990 penetrates and extends through this membrane 412 (and is held in this position by container adapter 920), thus allowing fluid within bottle 410 to contact, and enter through, an opening 994 in the distal end 995 of the syringe adapter (this opening 994 illustrated as being formed by the sidewall of syringe adapter 990 and located at the terminal end of distal end 995 and being generally blunt and frusto-conical in shape, as contrasted to the sharp end of a needle).

Figure 10D:
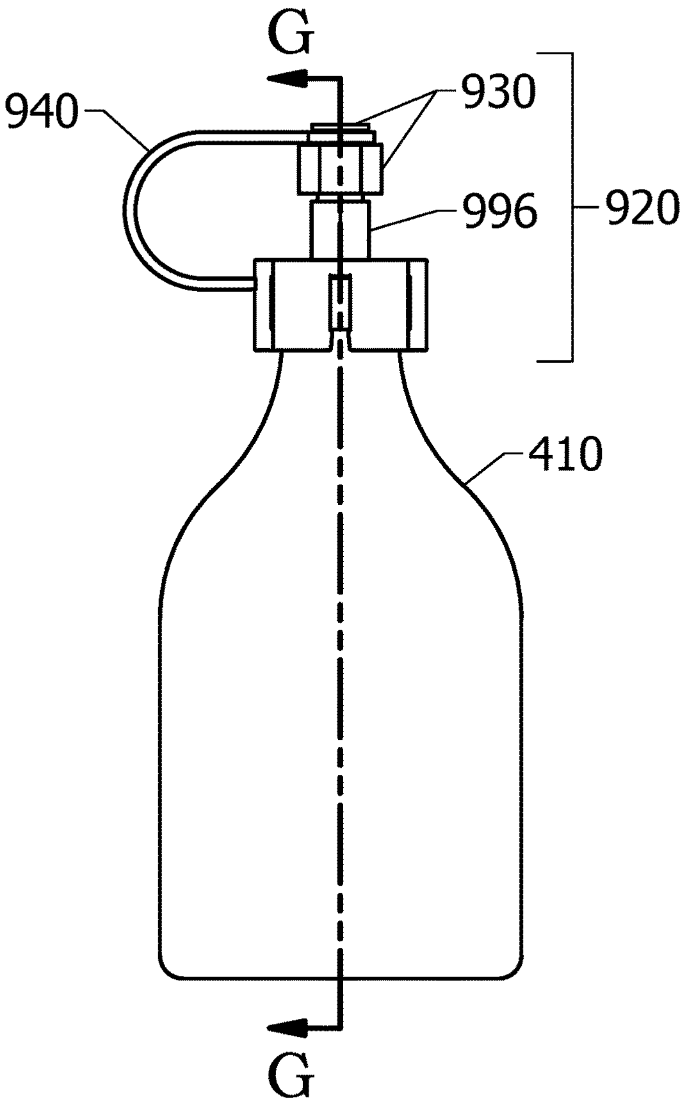
Figure 10E:
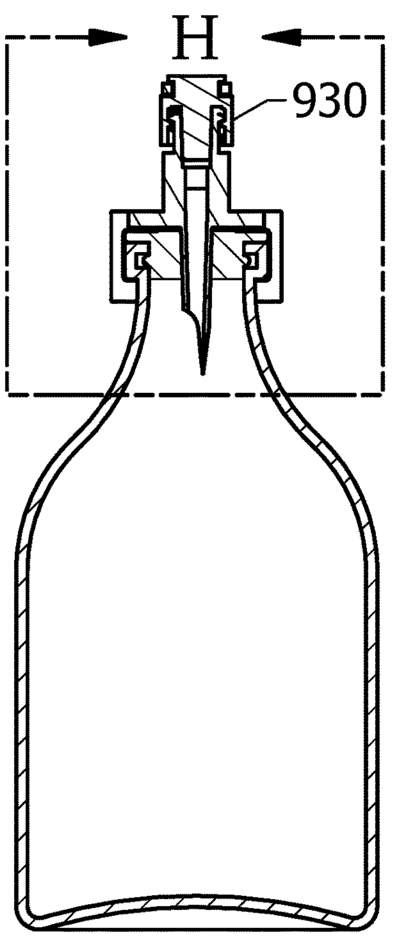
Figure 10F:
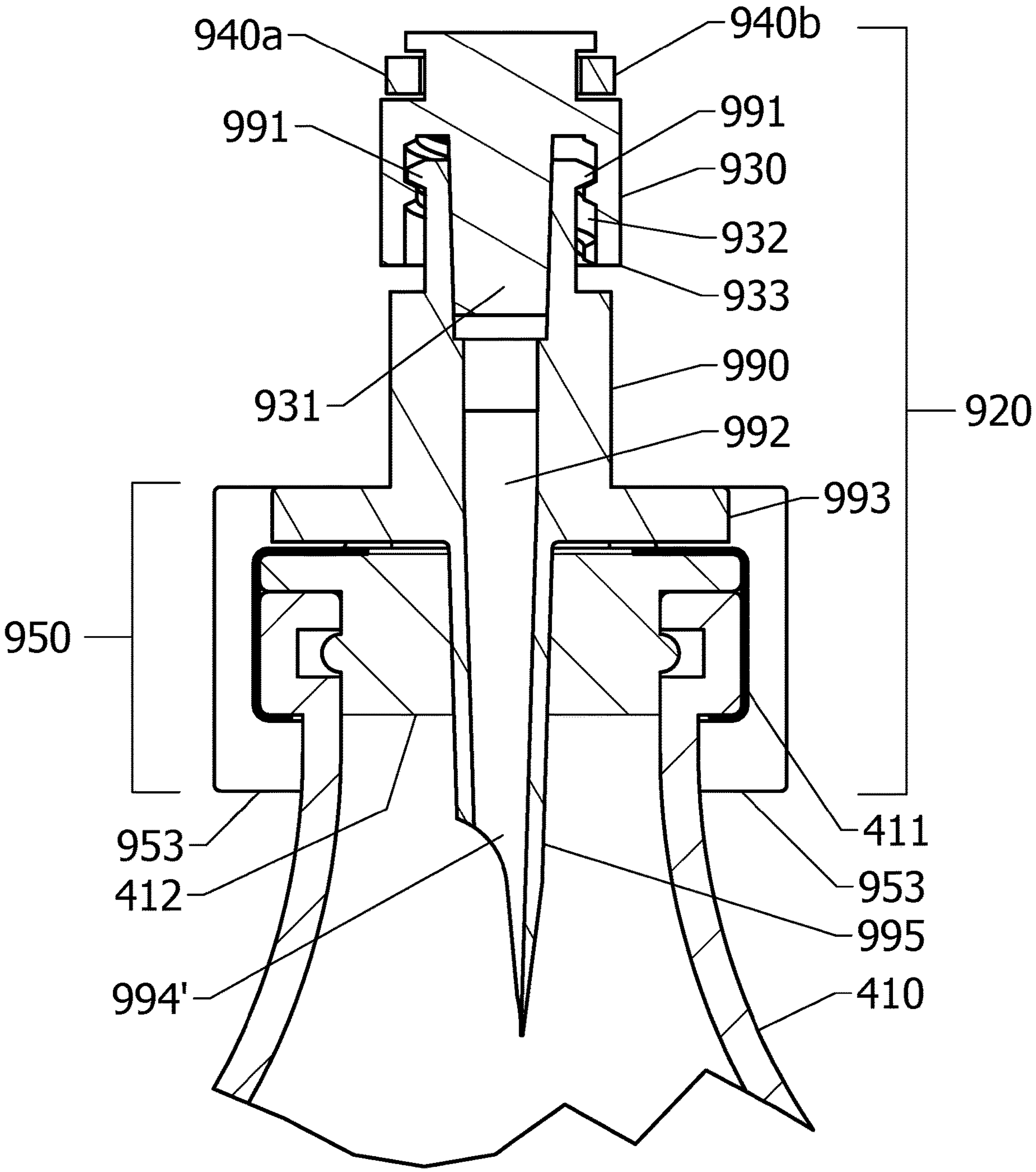
Figure 11:
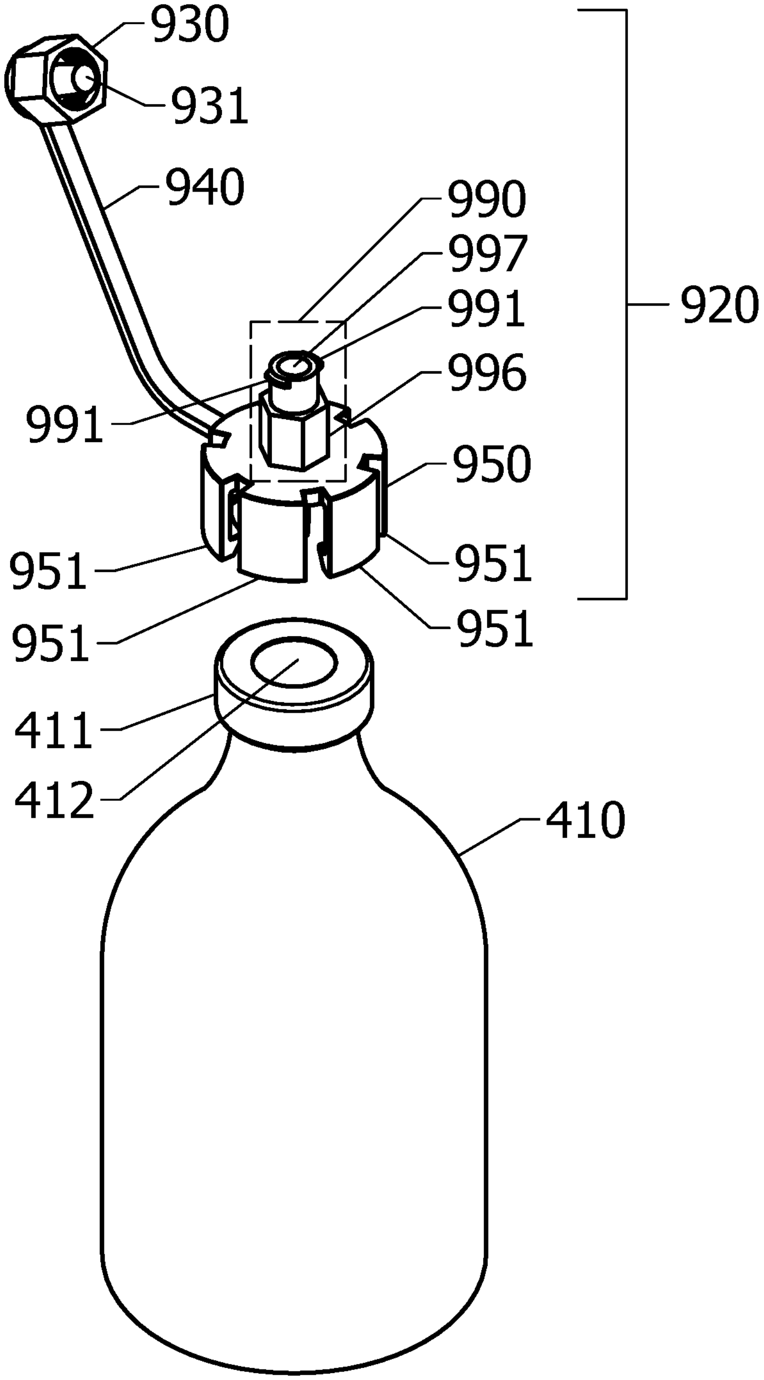
FIG. 11 illustrates an exploded view showing individual components of the assembly depicted in FIG. 9.

FIG. 11 illustrates an exploded view showing individual components of the assembly depicted in FIG. 9. A conventional bottle 410 is illustrated with its collar 411 and membrane 412. A syringe adapter 990 is illustrated, showing its flanged area 991 and proximal end opening 997. Extension 993, distal end 995, and the location therein of opening 994 are not visible in FIG. 11, but may be seen in FIGS. 10 and 13. As shown in FIG. 11, component 950 is designed with a plurality of sides 951 that are separated from one another, at and towards a terminal end, by a gap, these sides 951 preferably being connected (e.g., molded) to a top surface of component 950 at an edge opposite of their terminal end. Sides 951 are further configured as being somewhat flexible (i.e., at least able to bend or flex slightly outward, at their terminal ends, without breaking) and as having a lip area 953 (see FIGS. 10C and 13C) on their terminal end, thereby enabling the sides 951 to slip over collar 411 as component 950 is forced (e.g., pushed or pressed) onto collar 411, while also enabling the lip area 953 to then securably hook underneath collar 411 as lip area 953 reaches the underside of the collar 411 and the terminal ends of sides 951 then snap back into place after being bent/flexed. See FIGS. 12 and 13, where this attachment is illustrated (noting that portions of underlying collar 411 are visible in the gaps between sides 951). The attachment is preferably used as a permanent attachment, although if sides 951 are constructed from a material that can be severed, it would be possible to detach the container adapter 920 from bottle 410 if desired.

Figure 12:
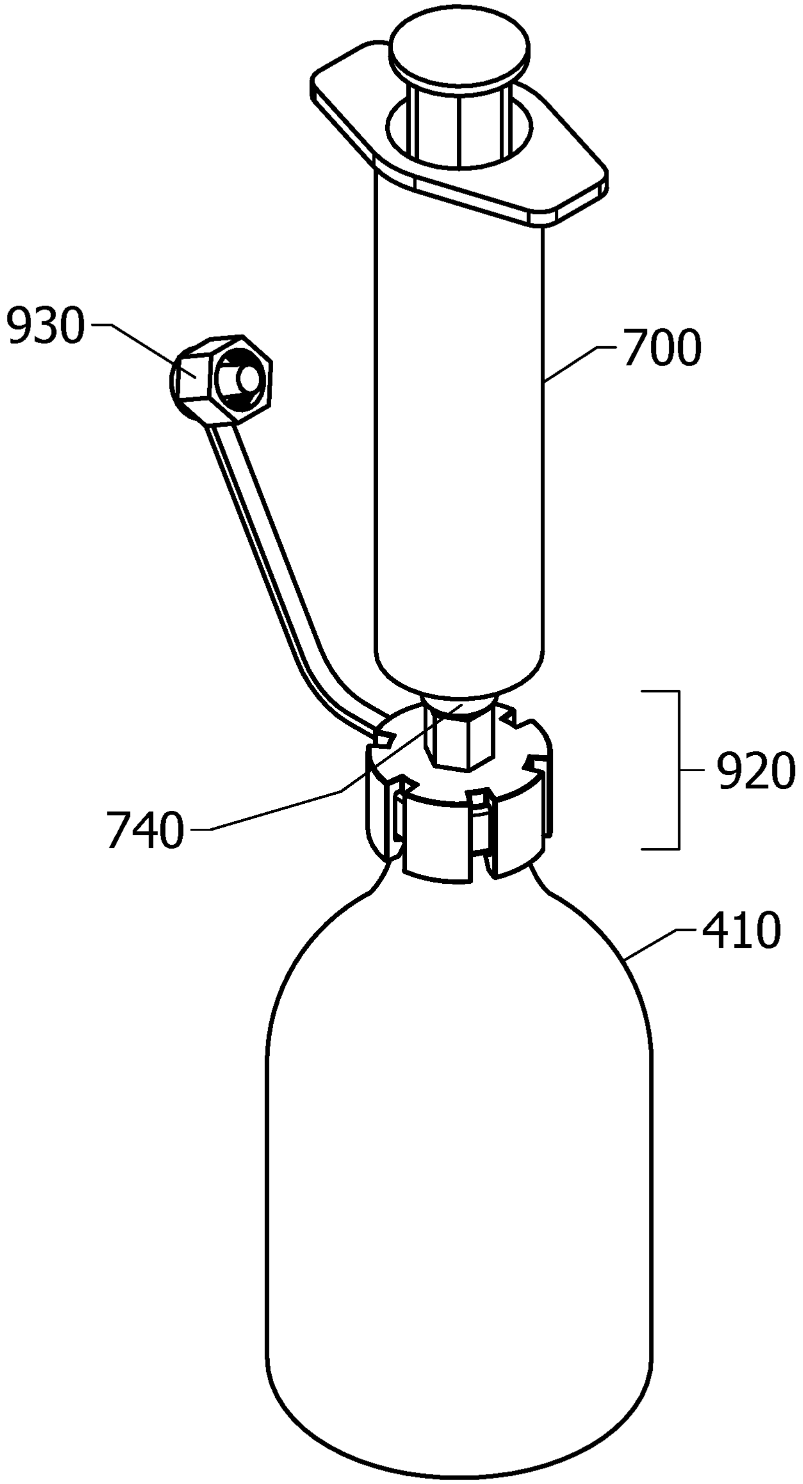
FIG. 12 illustrates an as-assembled perspective view of the container with container adapter fitted thereupon from FIG. 9, now illustrating how a syringe may be attached thereto.

FIG. 11 illustrates syringe adapter 990 extending through a top surface of component 950. In this example, syringe adapter 990 has a hexagonal exterior shape in at least a portion 996, and thus the top surface of component 950 adapts to this hexagonal shape. In a preferred approach, syringe adapter 990 is not separable from container adapter 920. Accordingly, it can be seen that syringe adapter 990 will not spin. Using a hexagonal (or more generally, multi-sided) exterior shape for portion 996 assists a person in easily grasping the syringe adapter 990—for example, when connecting syringe adapter 990 within the inner threaded area of cap 930 and/or (as shown in FIGS. 12 and 13) the inner threaded area of a syringe tip. (As will be obvious in view of teachings herein, if a syringe adapter is used that has a different shape for this exterior portion—for example, being cylindrical in shape or having a multi-sided exterior with a different number of sides—then the top surface of component 950 is preferably configured to match that exterior shape.)

FIG. 11 also illustrates cap 930 and its protrusion 931, the cap being attached to lanyard 940 which in turn is attached to component 950. Preferably, lanyard 940 is of sufficient length as to allow cap 930 to not interfere with other portions of the assembly when the cap is opened (as illustrated in FIG. 12).

FIG. 11 also illustrates how syringe adapter 990, in this embodiment, is preferably not separable from container adapter 920, as noted earlier. Instead, the container adapter 920 of this second embodiment is designed as an assembly that includes a syringe adapter 990 permanently attached to component 950. In one approach, this assembly may be performed in a manufacturing step. As an alternative to a permanent attachment between component 950 and syringe adapter 990, component 950 may be configured such that a syringe adapter 990 can be popped (or otherwise inserted) into an opening in a top surface thereof without deviating from the scope of the present invention. This inserting of a syringe adapter 990 into a component 950 may be performed during a manufacturing or distribution step. In another approach, inserting the syringe adapter 990 into the component 950 may be performed by a user. And as discussed above with reference to FIG. 6, assembly of the container adapter 920 (and its contained syringe adapter 990) onto a bottle 410 may be performed during manufacturing, distribution, or by a user.

As discussed above with reference to the first embodiment, syringe adapter 990 and other elements of container adapter 920 (including the cap 930, lanyard 940, and component 950) may be constructed from a plastic or a composite, or from another material such as stainless steel, aluminum, or another metal (or a combination thereof), without deviating from the scope of the present invention.

FIG. 12 illustrates an as-assembled perspective view of bottle 410 with container adapter 920 fitted thereupon from FIG. 9, now illustrating how a syringe 700 may be attached thereto. Refer to the above-provided description of syringe 700 and tip 740 for further information about the syringe and its tip.

FIG. 12 shows that cap 930 is now opened, and the tip 740 at the distal end of syringe 700 takes it place. Accordingly, a secure connection is made between tip 740 and the proximal end of syringe adapter 990 (this proximal end being contained inside tip 740 and thus not being visible in FIG. 12). FIG. 13 illustrates this secure connection in further detail.

Figures 13A, 13B:
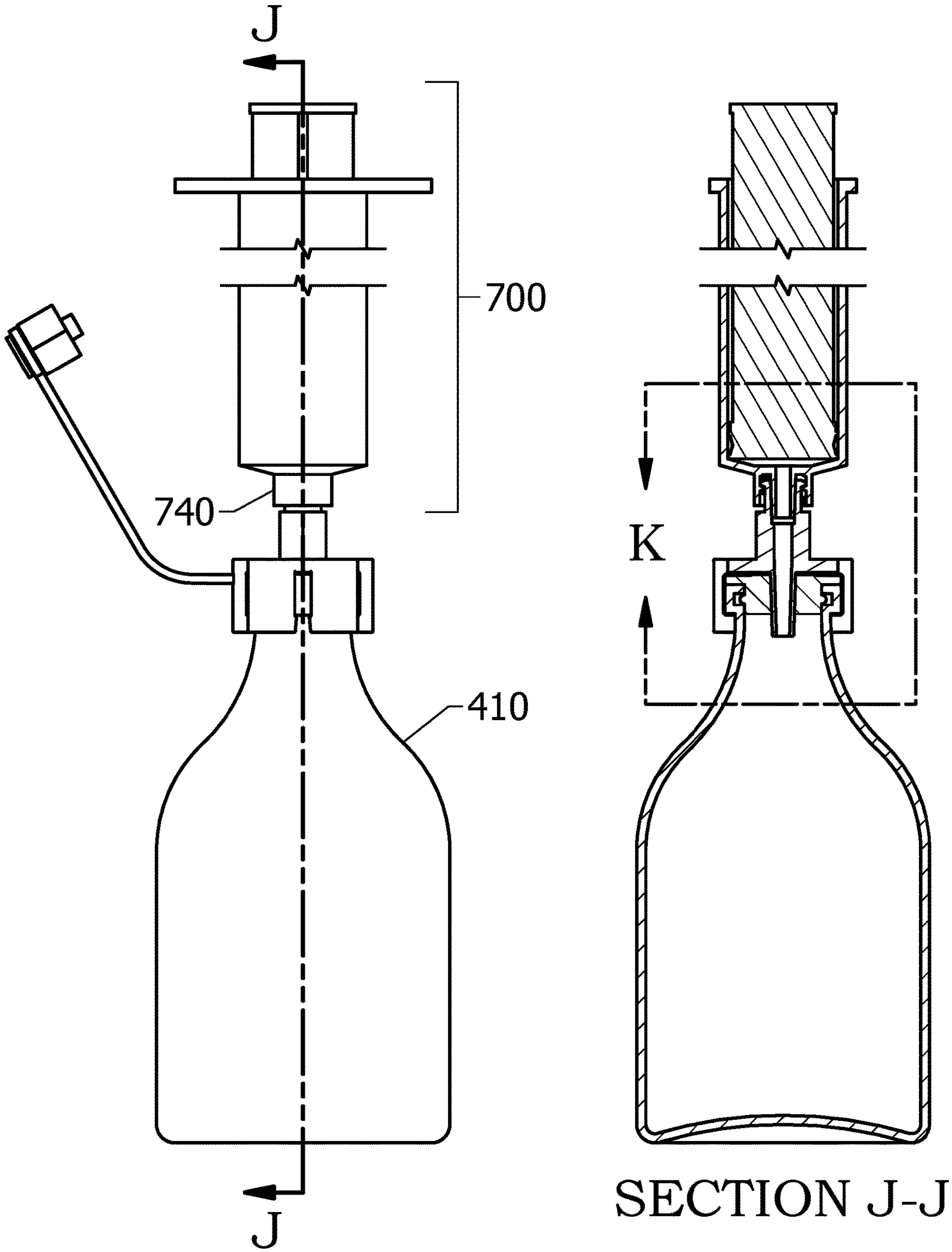
FIGS. 13A-13C depict further details of the assembly illustrated in FIG. 12, including a side view, a cross-sectional view along an imaginary line depicted using dashes in FIG. 13A, and a close-up view of a portion of the cross-sectional view, respectively, and FIGS. 13D-13F provide a variation on the illustrations in FIGS. 13A-13C, respectively.
Figure 13C:
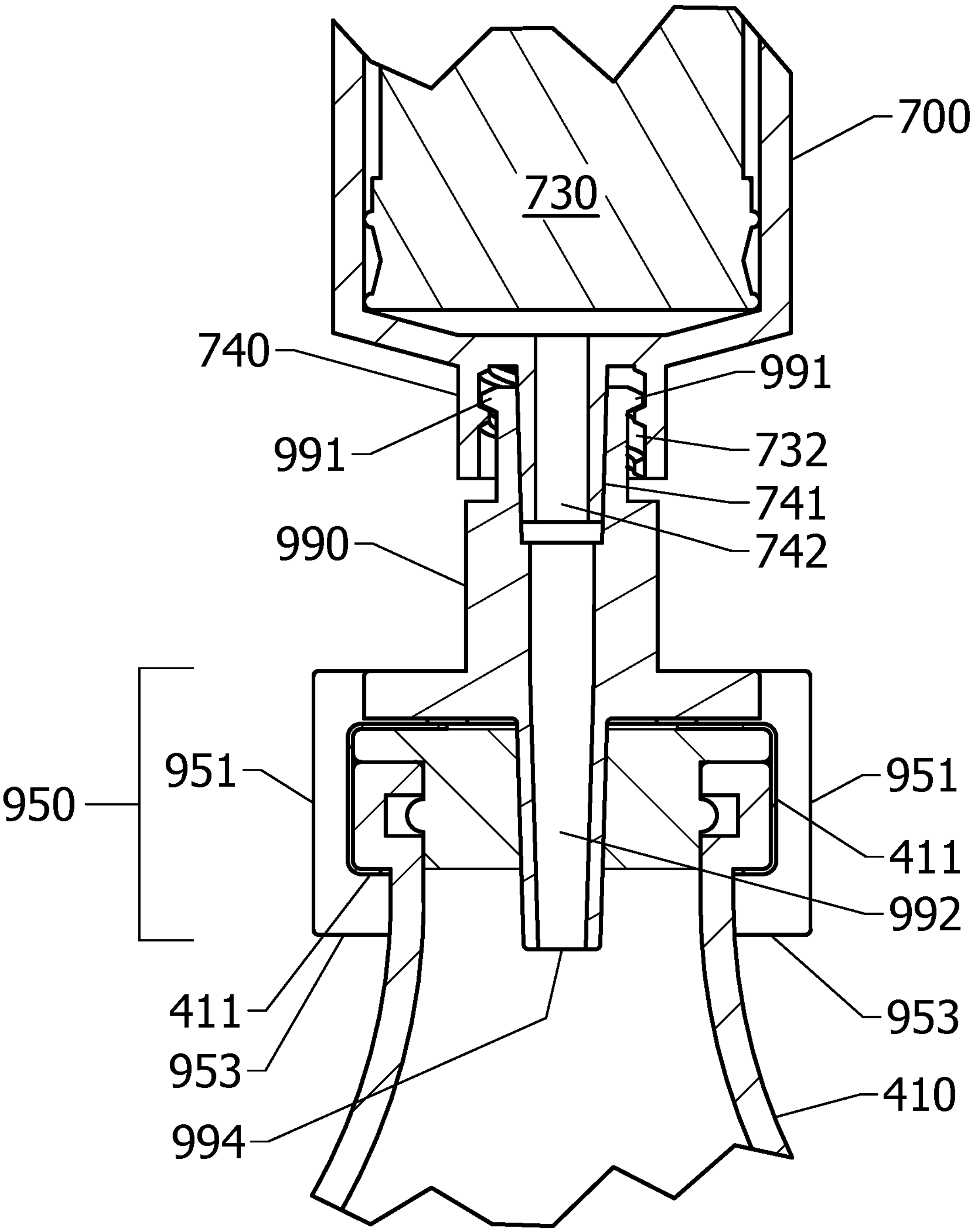

FIG. 13A illustrates a side view of the assembly shown in FIG. 12, with syringe 700 attached to bottle 410. FIG. 13B provides a cross-sectional view along an imaginary line that is denoted as "J" and depicted using dashes in FIG. 13A. FIG. 13C provides a close-up view of a portion of the cross-sectional view of FIG. 13B, this portion denoted as "K" in FIG. 13B, and for ease of reference, discussions will now refer to the close-up view in FIG. 13C.

FIG. 13C shows the component 950 of the container adapter, with its sides 951 and their lip areas 953, surrounding collar 411 to thereby secure the container adapter 920 to the bottle 410 while encapsulating syringe adapter 990, as has been discussed above with reference to FIG. 10C. FIG. 13C differs from FIG. 10C, however, in that the cap 930 is now opened and replaced with syringe 700 as noted above with reference to FIG. 12. FIG. 13C shows how syringe 700 is securably attached to syringe adapter 990, this attachment comprising inserting flanged area 991 into corresponding internal threads of threaded area 732 shown in the interior of syringe tip 740 and then twisting until flanged area 991 of the syringe adapter 990 locks into place within threaded area 732. As can be seen in FIG. 13C, the proximal end of syringe adapter 990 is preferably sized—as disclosed in one or more of the related applications—so as to slip over the protrusion 741 while at the same time, fitting within the threaded interior area 732 of syringe tip 740. (As noted above and as discussed in one or more of the related applications, inner and outer diameters of the proximal end—i.e., the end where reference number 991 is generally pointing—are preferably designed for compatibility with such measurements to enable syringe adapter 990 to make a secure attachment to the internal threaded area 732 of a syringe tip 740 that is manufactured in conformance with measurements provided in the above-cited International Standard ISO 80369-7.)

FIG. 13C depicts, in detail, how a fluid path exists for withdrawing fluid from bottle 410 through the opening 994 into the syringe adapter 990, then through the hollow chamber 992 of the syringe adapter 990, then through proximal end opening 997 (shown in FIG. 11) of the syringe adapter where it meets with an opening shown generally at 742 of protrusion 741, and finally into the barrel 730 of syringe 700. Because the disclosed container adapter securably connects all of the elements as illustrated in FIG. 13 (i.e., syringe, syringe adapter, and bottle), a user now has fewer things to hold and to manage during the withdrawal process and may therefore be less likely to experience problems while withdrawing fluid, as was noted earlier.

Figure 13D:
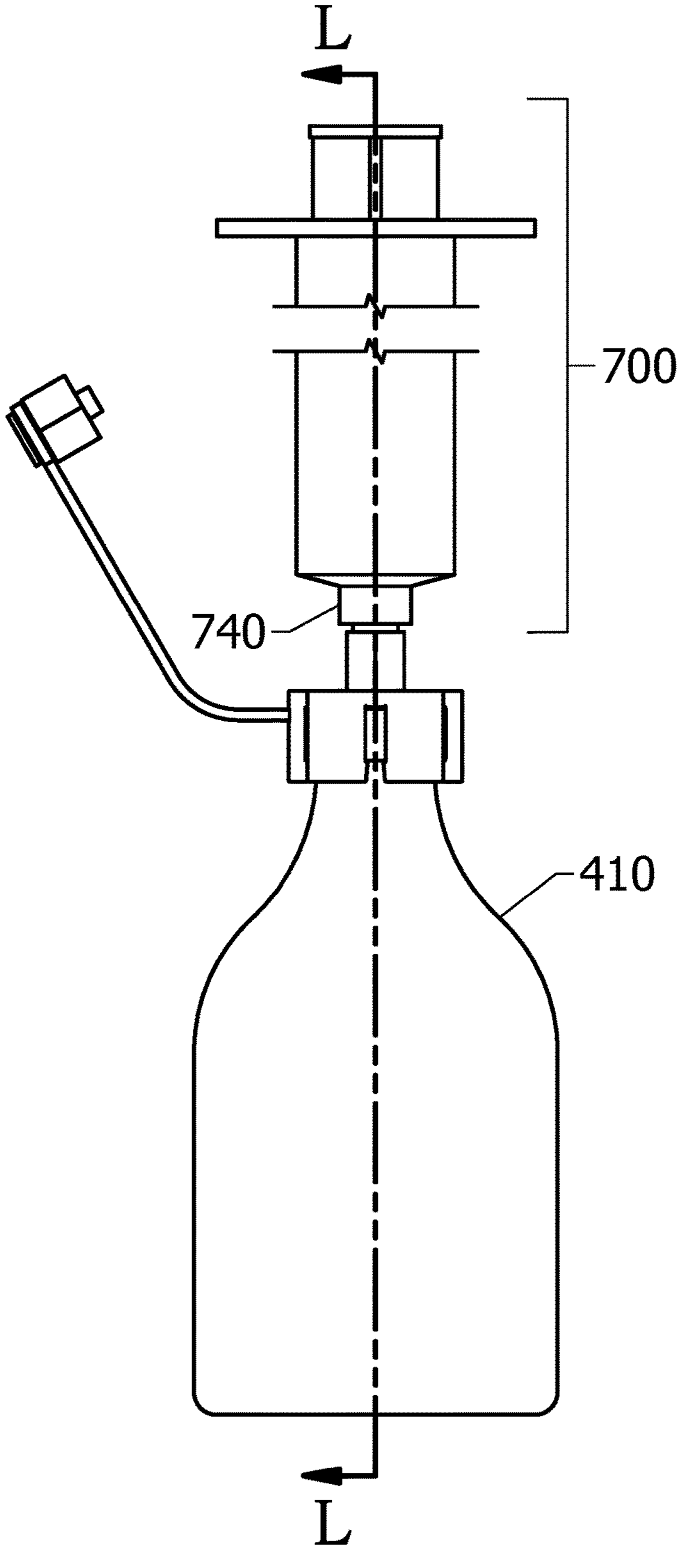
Figure 13E:
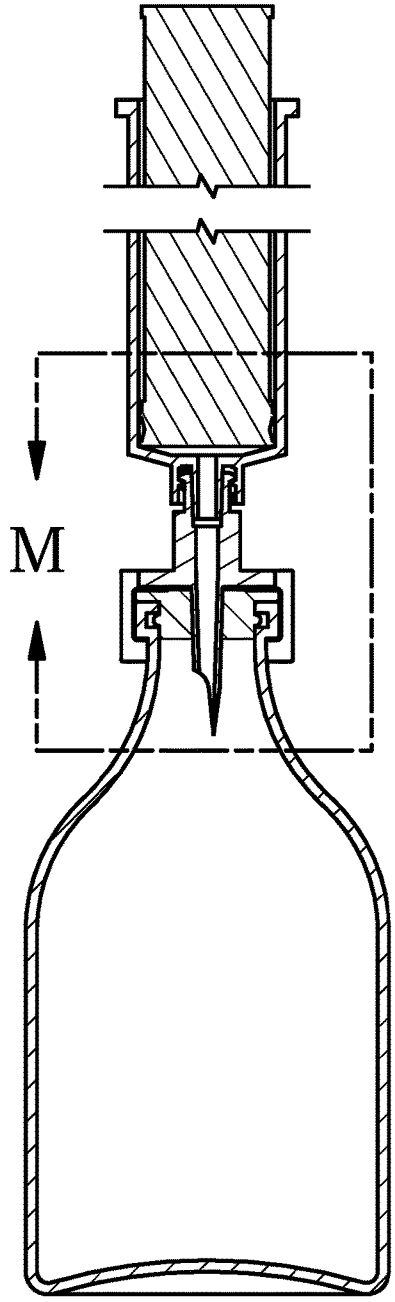
Figure 13F:
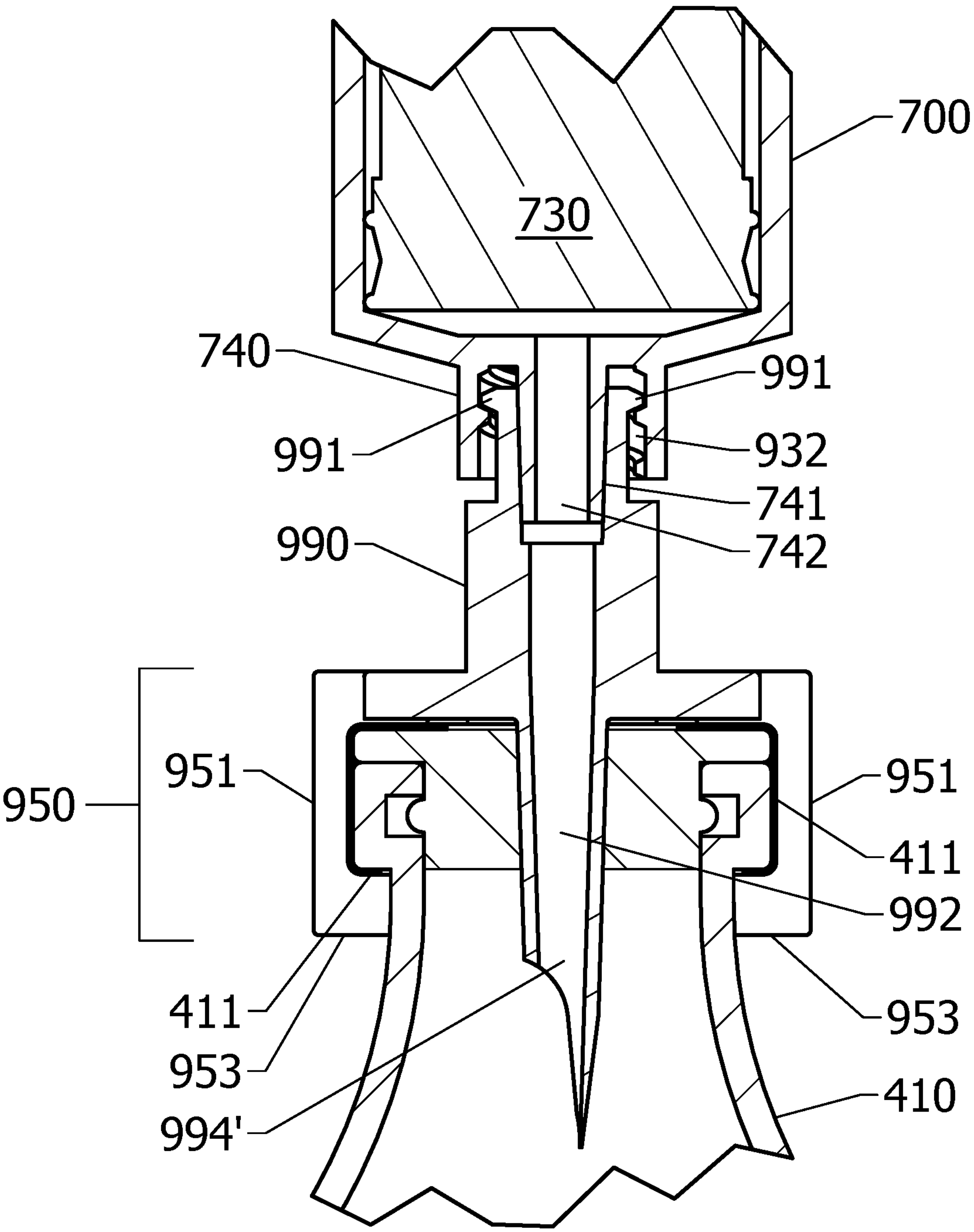

FIGS. 10D-10F provide a variation on the illustrations in FIGS. 10A-10C, respectively, and FIGS. 13D-13F provide a variation on the illustrations in FIGS. 13A-13C, respectively, as will now be discussed.

The related applications disclose embodiments where the distal end of the syringe adapter is generally blunt (and frusto-conical in shape) at the opening, as contrasted to the sharp end of a needle. The related applications also disclose embodiments where the distal end of the syringe adapter has a relatively sharp tip. Any of the container adapter embodiments as disclosed herein may be used with a syringe adapter having either of these configurations. Because a container adapter according to the second embodiment is preferably manufactured to include a syringe adapter, as noted earlier, illustrations are provided in FIGS. 10D-10F and 13D—13F showing how the container adapter and its syringe adapter differs in physical appearance when the syringe adapter has a relatively sharp tip at the distal end. The alternative distal end opening is denoted in these figures with reference number 994'. (While syringe adapters with this configuration at the distal end are not separately illustrated for the first and third embodiments, one of ordinary skill in the art will readily understand, in view of teachings herein, how illustrations for those embodiments would be modified for the alternative configuration. Such configuration may be used in those embodiments without deviating from the scope of the present invention.)

FIGS. 14-18 illustrate a third embodiment of the container adapter disclosed herein.

Figure 14:
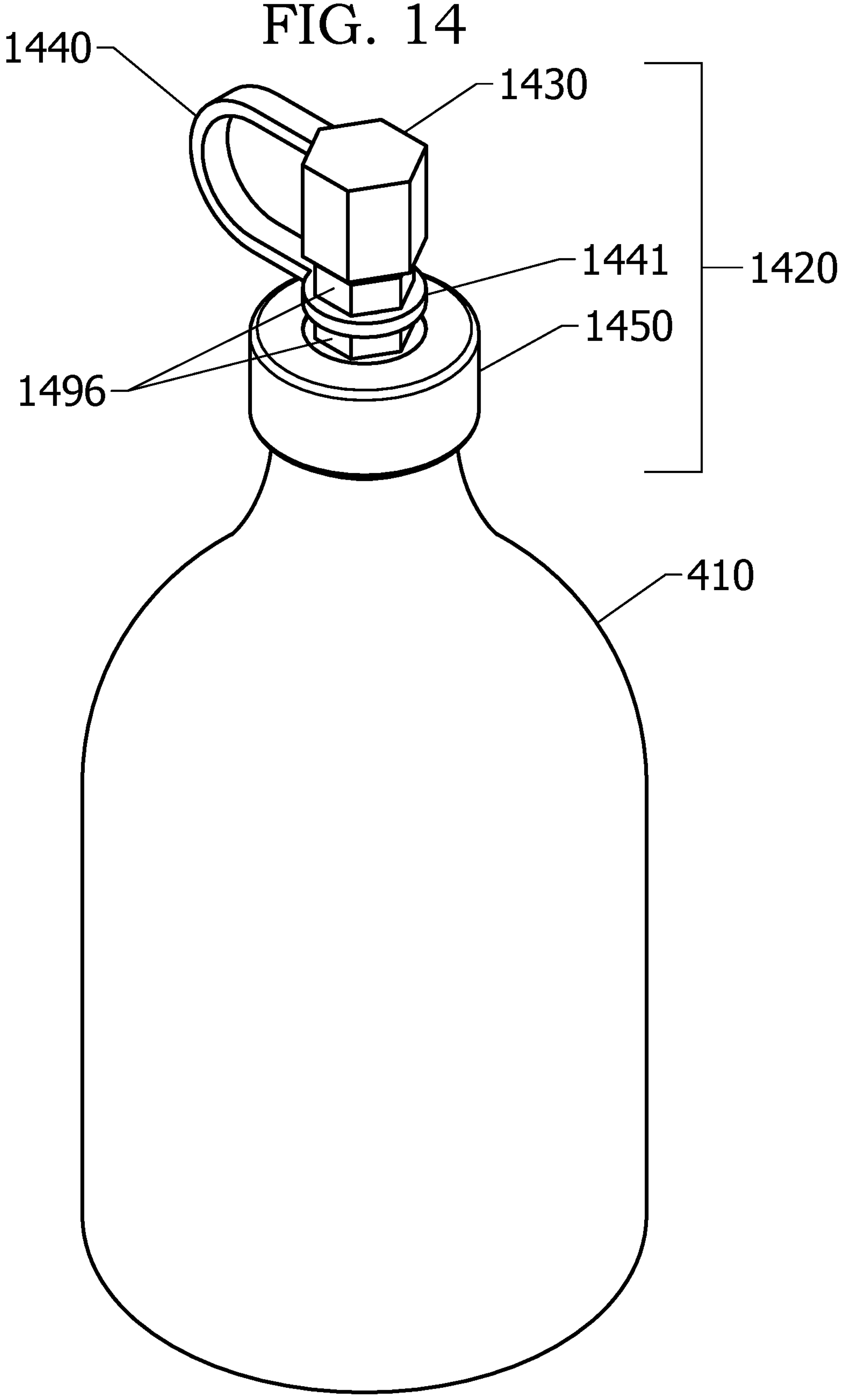
FIG. 14 depicts an as-assembled view of a container with container adapter fitted thereupon, according to a third embodiment of the present invention, and is shown as a perspective view.

FIG. 14 depicts an as-assembled view of a bottle 410 with a container adapter 1420 fitted thereupon, the container adapter 1420 securing therein a syringe adapter 1490 (as shown in further detail in FIGS. 15-18). A cap 1430 is shown as being closed, thus preventing fluid in bottle 410 from leaking or spilling out. A lanyard 1440 is attached to the cap 1430. In this embodiment, a ring 1441 is attached to the other end of lanyard 1440 (see also FIG. 16), and is depicted as being placed within an indentation or groove 1498 (see FIG. 16) in a portion 1496 of an exterior of syringe adapter 1490. A component 1450 is also provided, along with a stopper 1460 contained therein (stopper 1460 not being visible in FIG. 14). These elements are assembled so as to securely hold a syringe adapter 1490, as will now be discussed in more detail with reference to FIGS. 15 and 16. (Syringe adapter 1490 may be similar, including identical, to syringe adapter 490 or 990. Cap 1430 and lanyard 1440 may also be similar to cap 430 or 930 and lanyard 440 or 940, although it is preferred that cap 1430 and lanyard 1440 are configured as shown in FIG. 14.)

Figure 15A:
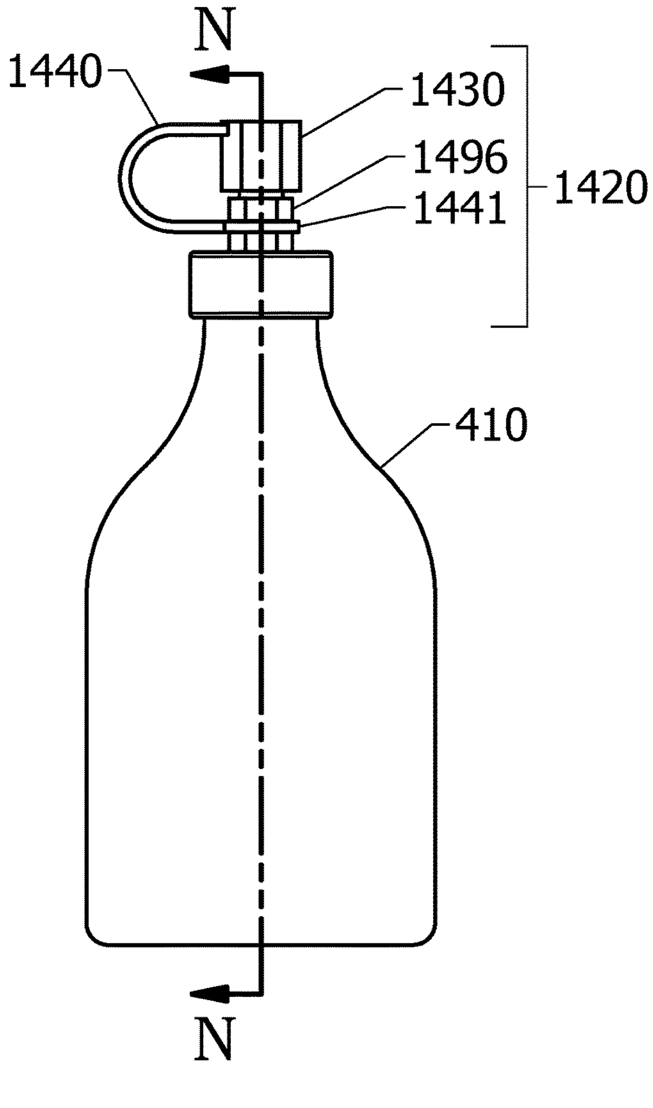
FIG. 15 (comprising FIGS. 15A-15C) illustrates a side view, a cross-sectional view along an imaginary line depicted using dashes in FIG. 15A, and a close-up view of a portion of the cross-sectional view, respectively, according to the third embodiment.
Figure 15B:
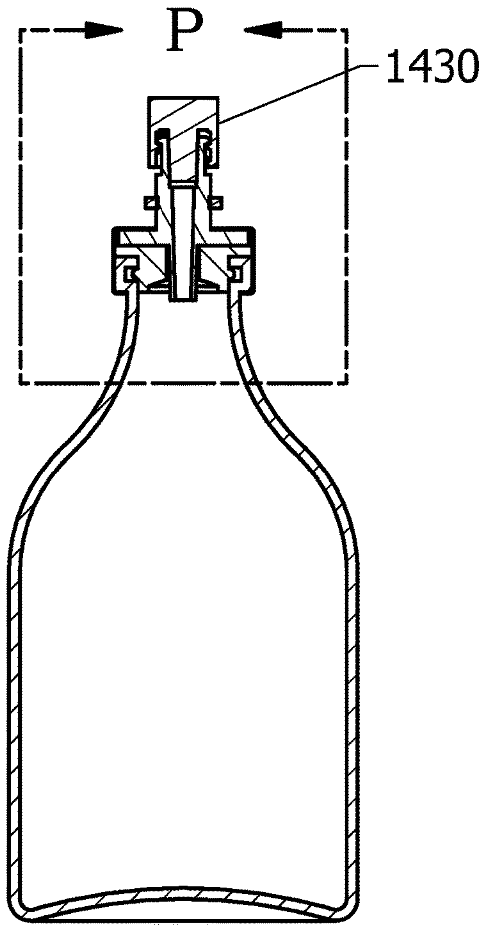
Figure 15C:
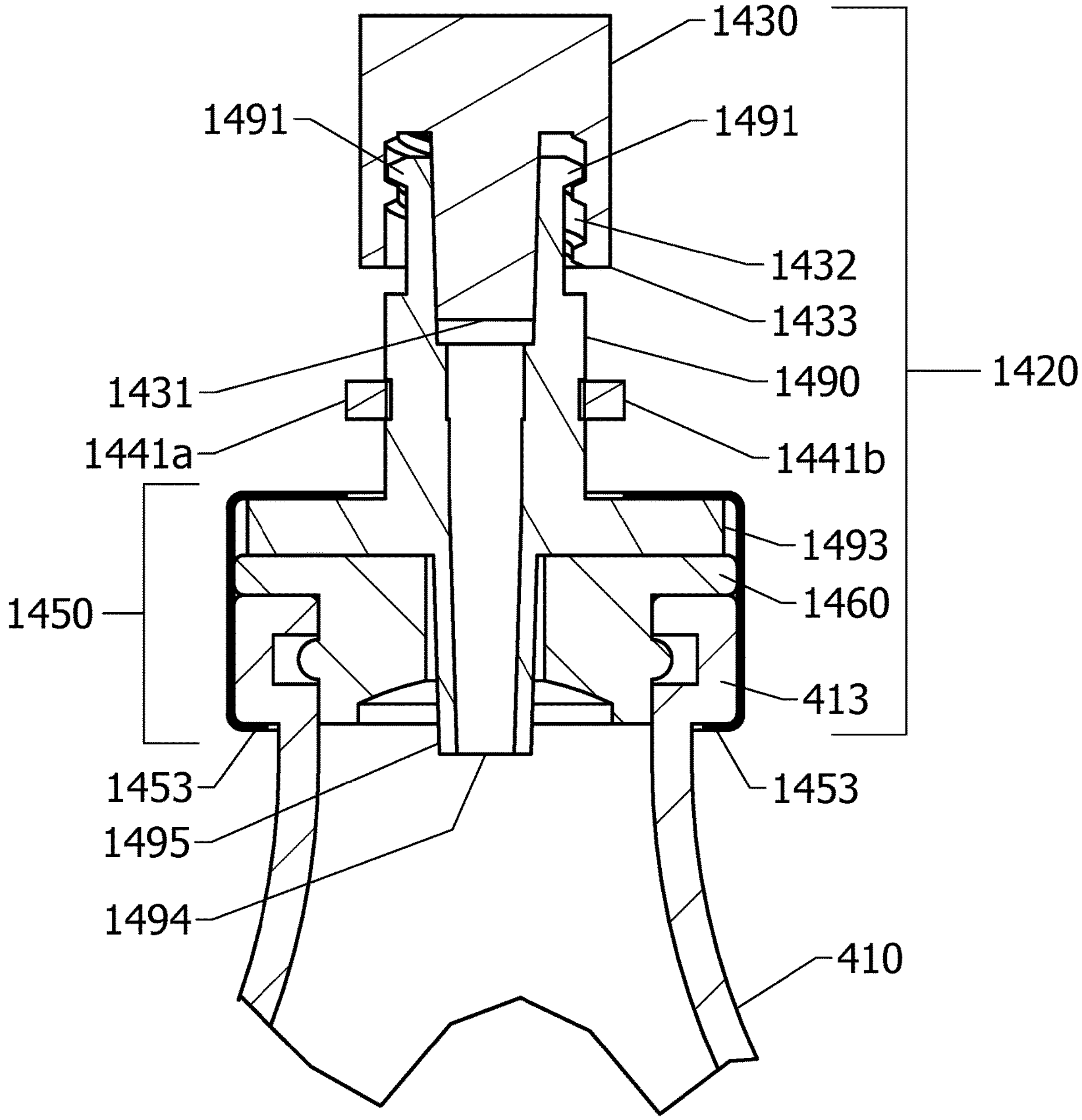

FIG. 15A illustrates a side view of this third embodiment, showing container adapter 1420 placed upon bottle 410. FIG. 15B provides a cross-sectional view along an imaginary line that is denoted as "N" and depicted using dashes in FIG. 15A. FIG. 15C provides a close-up view of a portion of the cross-sectional view of FIG. 15B, this portion denoted as "P" in FIG. 15B, and for ease of reference, discussions will now refer to the close-up view in FIG. 15C.

FIG. 15C illustrates how cap 1430 is placed on (i.e., removably connected to) a syringe adapter 1490, thus closing off entry and exit into bottle 410. Preferably, portions of cap 1430 are configured to mimic portions of a syringe tip from a conventional syringe. More particularly, cap 1430 is depicted as having a protruding tip 1431 and a threaded inner attachment area 1432. (Notably, tip 1431 does not have a through-hole, as distinguished from a conventional syringe tip.) In the approach depicted in FIG. 15C, the tip 1431 protrudes somewhat from an edge 1433 of cap 1430 and into the hollow chamber 1492 of the syringe adapter 1490. (Note that while chamber 1492 is illustrated as having a generally cylindrical shape at one end and a generally conical or tapered shape at the other end, and that while syringe adapter 1490 is illustrated as having particular dimensions, this is by way of illustration but not of limitation, and an embodiment of the disclosed container adapter may be suitably configured to accommodate varying outer shapes and dimensions of syringe adapters without deviating from the scope of the present invention.)

Cap 1430 is preferably configured with a multi-sided exterior (shown in FIGS. 14-18 as being hexagonal, by way of illustration but not of limitation). This multi-sided exterior shape enables a user to twist and/or grip the cap with relative ease. Accordingly, a secure and leak-free Luer-type lock connection between cap 1430 and syringe adapter 1490 may be made by rotating/twisting cap 1430 (and/or syringe adapter 1490) until a flanged area 1491 extending laterally from a proximal end of syringe adapter 1490 (i.e., the end where reference number 1491 is generally pointing) moves within internal threaded area 1432 of cap 1430 until flanged area 1491 locks into place within threaded area 1432. Notably, this is the same approach for making a leak-free connection that will preferably be used when connecting a syringe to the syringe adapter 1490 (as will be discussed in further detail with reference to FIGS. 17 and 18). As noted earlier, a conventional height for the internal threaded portion of a tip of a pistol-grip or tab-handled syringe is believed to be approximately ⅛ inch to ¼ inch in length and a standardized height thereof is believed to be 5.4 millimeters to conform with the above-cited International Standards. Accordingly, threaded area 1432 of cap 1430 preferably has a similar height so as to accommodate flanged area 1491 on the proximal end of syringe adapter 1490 (where a height of flanged area 1491, as described in the related applications, is preferably on the order of at least 1/16 to ⅛ inch in height in view of the height of the syringe tip threads).

Figure 16:
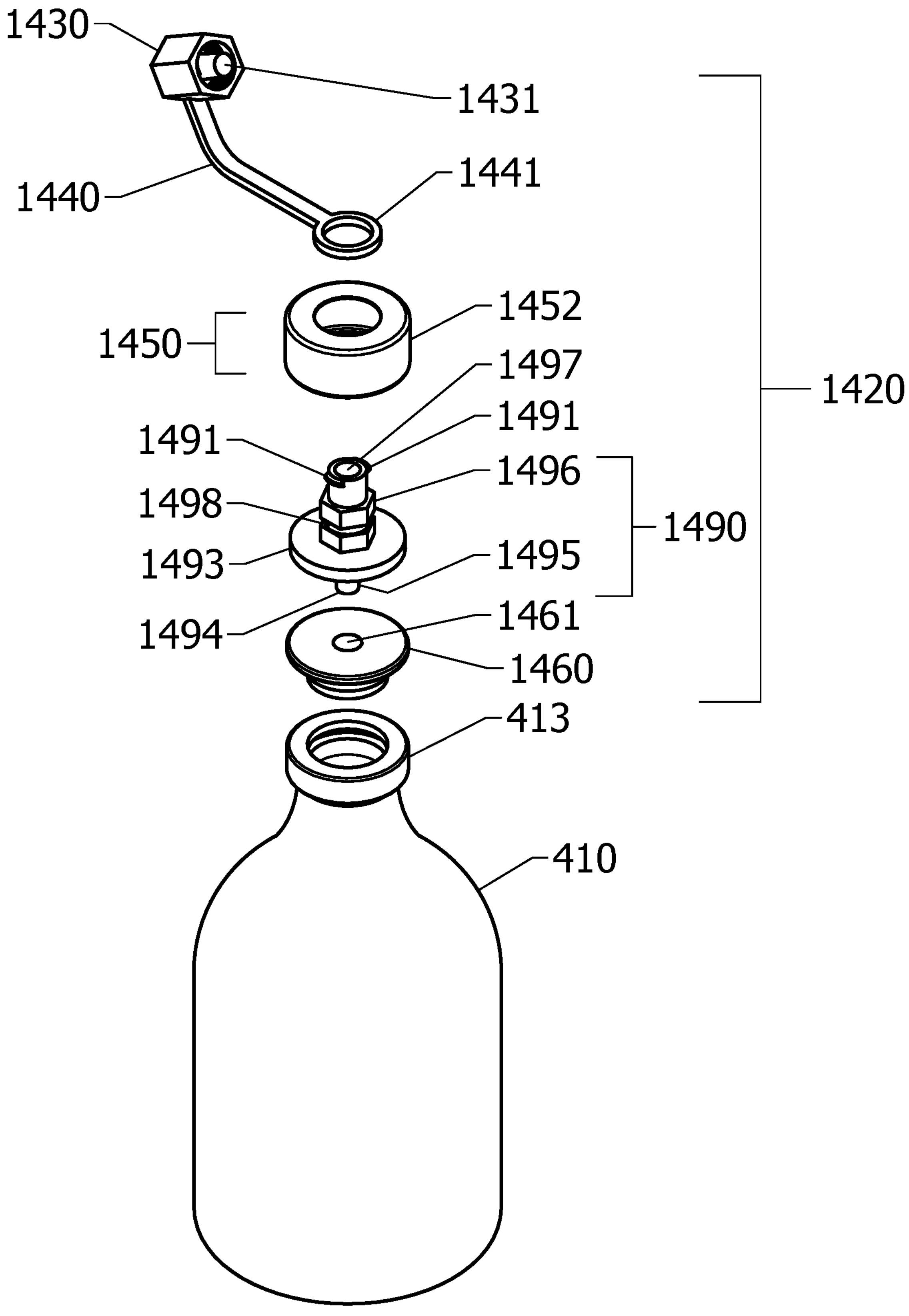
FIG. 16 illustrates an exploded view showing individual components of the assembly depicted in FIG. 14.

Reference numbers 1441*a*, 1441*b* represent portions of the ring-shaped end 1441 of lanyard 440 as its surrounds, and sits in the indentation 1498 of, portion 1496 of syringe adapter 1490 (see also FIG. 16).

Reference number 413 depicts a conventional edge surrounding a neck opening on bottle 410, and FIG. 15C illustrates how component 1450 is designed to surround this neck opening edge 413 to thereby secure the container adapter 1420 (and thus the syringe adapter 1490) to the bottle 410. Notably, the collar 411 that was discussed above is not present in this embodiment, as collar 411 generally serves to hold a membrane in place over a neck opening of a conventional bottle. In this embodiment, rather than hooking underneath a collar 411 that is itself surrounding a neck opening edge of a bottle, component 1450 is secured directly to neck opening edge 413 by a lip area 1453 configured on the lower edge of component 1450 and a stopper 1460, the lip area 1453 configured to securably hook underneath neck opening edge 413 while stopper 1460 attaches (e.g., by pressing in as a plug or gasket) to an interior of the neck opening. Bottle 410 is typically constructed from glass, as noted earlier, in which case neck opening edge 413 of a prior art bottle 410 typically comprises a relatively thickened area of glass; alternatively, bottle 410 and neck opening edge 413 may be constructed from a different material without deviating from the scope of the present invention. An inner diameter of component 1450 is preferably only slightly larger than the diameter of an exterior of neck opening edge 413. In this manner, component 1450 will fit snugly around neck opening edge 413, and will be less likely to slip or spin. Similarly, a height of component 1450—including lip area 1453—is preferably sized to enable a secure fit by being only slightly taller than a sum of the height of neck opening edge 413, an upper portion of stopper 1460 that rests upon an upper surface of neck opening edge 413, and the height of extension 1493 (as shown in FIGS. 15C and 18C).

FIG. 15C also illustrates how container adapter 1420 is configured to encapsulate an extension 1493 of syringe adapter 1490, extension 1493 being configured in this example as a radial extension. (Note that while the extension 1493 is illustrated as being round at its perimeter, and the exterior dimension thereof is shown as fully extending within the bounds of the interior diameter of component 1450, this is by way of illustration but not of limitation.) A conventional bottle 410 typically includes a rubber membrane covering at least a portion of an opening at the top of the bottle and the rubber membrane typically has a dimple in the center where it is intended for the rubber membrane to be penetrated, as noted earlier. In this embodiment, a stopper 1460 is used, and is inserted into a neck opening of bottle 410 to thereby plug the neck opening (as shown also in FIG. 16). Preferably, stopper 1460 is placed beneath extension 1493, and rests above an upper surface of neck opening edge 413, as shown in FIG. 15C. A distal end 1495 of syringe adapter 1490 penetrates and extends through a hole 1461 in this stopper 1460 (the hole 1461 being illustrated in FIG. 16) and is held in this position by container adapter 1420, thus allowing fluid within bottle 410 to contact, and enter through, an opening 1494 in the distal end 1495 of the syringe adapter (this opening 1494 illustrated as being formed by the sidewall of syringe adapter 1490 and located at the terminal end of distal end 1495 and being generally blunt and frusto-conical in shape, as contrasted to the sharp end of a needle).

Figure 17:
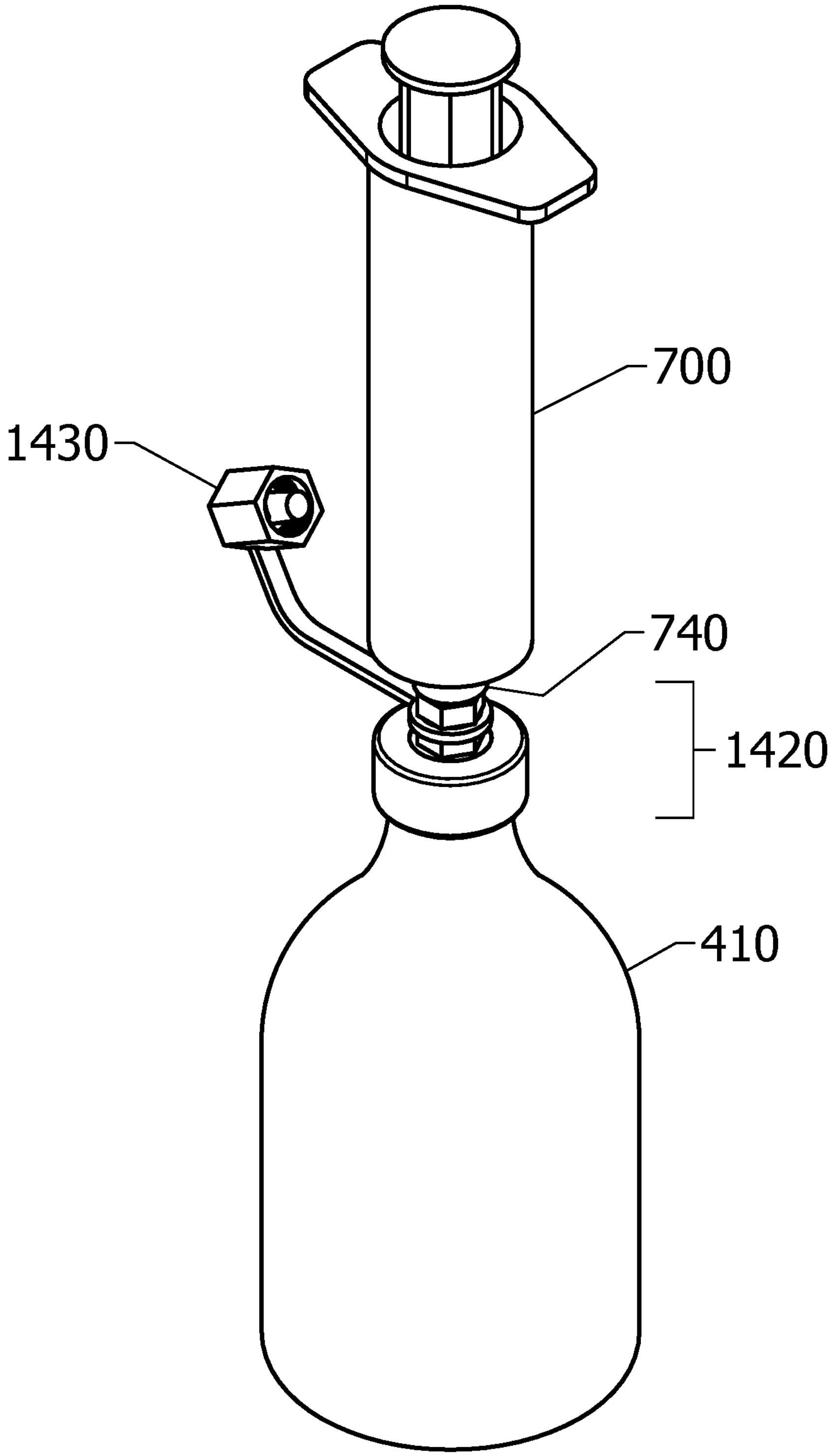
FIG. 17 illustrates an as-assembled perspective view of the container with container adapter fitted thereupon from FIG. 14, now illustrating how a syringe may be attached thereto.

FIG. 16 illustrates an exploded view showing individual components of the assembly depicted in FIG. 14. A conventional bottle 410 is illustrated, although as noted above, a conventional collar and membrane (such as collar 411 and membrane 412 of FIGS. 6 and 11) are not present on bottle 410 in this embodiment; instead, component 1450 and stopper 1460 are provided in this embodiment. A syringe adapter 1490 is illustrated, showing its flanged area 1491, proximal end opening 1497, extension 1493, distal end 1495, and the location therein of opening 1494. Reference number 1498 illustrates the indentation in portion 1496. Component 1450 is shown as having a cylindrical shape with an opening at a top and bottom surface thereof, these openings preferably being round and being smaller in diameter than a sidewall 1452 that forms the outer edge of the cylindrical shape. As can be seen by the illustration in FIG. 16 (with further reference to FIGS. 15C, 17, and 18C), a diameter of the opening in the top surface of component 1450 must be at least large enough to accommodate the largest diameter of the proximal end 1496 of the syringe adapter, while the opening in the bottom surface of component 1450 must be large enough to accommodate the larger of (i) the diameter of the extension 1493 and (ii) the diameter of the outer surface of neck opening edge 413. As an alternative to having a round opening in the top surface of component 1450, this opening may be multi-sided, such as hexagonal, if desired to conform to a corresponding multi-sided exterior shape of a portion 1496 of syringe adapter 1490 so that the syringe adapter does not spin. Using a hexagonal (or more generally, multi-sided) exterior shape for portion 1496 assists a person in easily grasping the syringe adapter 1490—for example, when connecting syringe adapter 1490 within the inner threaded area of cap 1430 and/or (as shown in FIGS. 17 and 18) the inner threaded area of a syringe tip. (As will be obvious in view of teachings herein, if a syringe adapter is used that has a different shape for this exterior portion—for example, being cylindrical in shape or having a multi-sided exterior with a different number of sides—then the opening in the top surface of component 1450 may be configured to match that exterior shape.)

FIG. 16 also illustrates cap 1430 and its protrusion 1431, the cap being attached to lanyard 1440 opposite its ring-shaped end 1441. Preferably, lanyard 1440 is of sufficient length as to allow cap 1430 to not interfere with other portions of the assembly when the cap is opened (as illustrated in FIG. 17).

As illustrated in FIG. 16, the container adapter 1420 of this third embodiment is designed as pieces to be assembled over, and under, a syringe adapter 1490, with the assembly then placed on, and extending into, the neck opening surrounded by edge 413. Preferably, this assembly is performed in a manufacturing step, as part of a process that fills the bottle with fluid. A crimping (or similar) process preferably secures component 1450 to neck opening edge 413, in a similar manner to how bottles are conventionally distributed with collar 411 (see, for example, FIGS. 6 and 11) placed over this neck opening edge. Accordingly, attachment of container adapter 1420 to bottle 410 is preferably a permanent attachment. Users thus receive a bottle that is fully configured with a container adapter 1420 and the syringe adapter 1490 contained therein. (In another approach, this assembly is performed by a user, thus enabling the user to attach the container adapter—and the syringe adapter it secures—to a suitably-sized bottle. In this latter approach, the pieces of the container adapter and its syringe adapter may be packaged together so that the user receives all needed components; as an alternative, components of the container adapter may be provided separately, such that (for example) a user receives component 1450, stopper 1460, and lanyard 1440 with cap 1430 attached thereto, and then provides his or her own syringe adapter during the assembly process. This approach is not preferred, at least for the reason that the user may accidentally cause the fluid contained in the bottle to leak therefrom.)

As discussed above with reference to the first and second embodiments, elements of container adapter 1420 (including the cap 1430, lanyard 1440, ring 1441, and syringe adapter 1490) may be constructed from a plastic or a composite, or from another material such as stainless steel, aluminum, or another metal (or a combination thereof), without deviating from the scope of the present invention. Component 1450 is preferably constructed from metal. Stopper 1460 is preferably constructed from rubber.

FIG. 17 illustrates an as-assembled perspective view of bottle 410 with container adapter 1420 fitted thereupon from FIG. 14, now illustrating how a syringe 700 may be attached thereto. Refer to the above-provided description of syringe 700 and tip 740 for further information about the syringe and its tip.

FIG. 17 shows that cap 1430 is now opened, and the tip 740 at the distal end of syringe 700 takes it place. Accordingly, a secure connection is made between tip 740 and the proximal end of syringe adapter 1490 (this proximal end being contained inside tip 740 and thus not being visible in FIG. 17). FIG. 18 illustrates this secure connection in further detail.

Figure 18A:
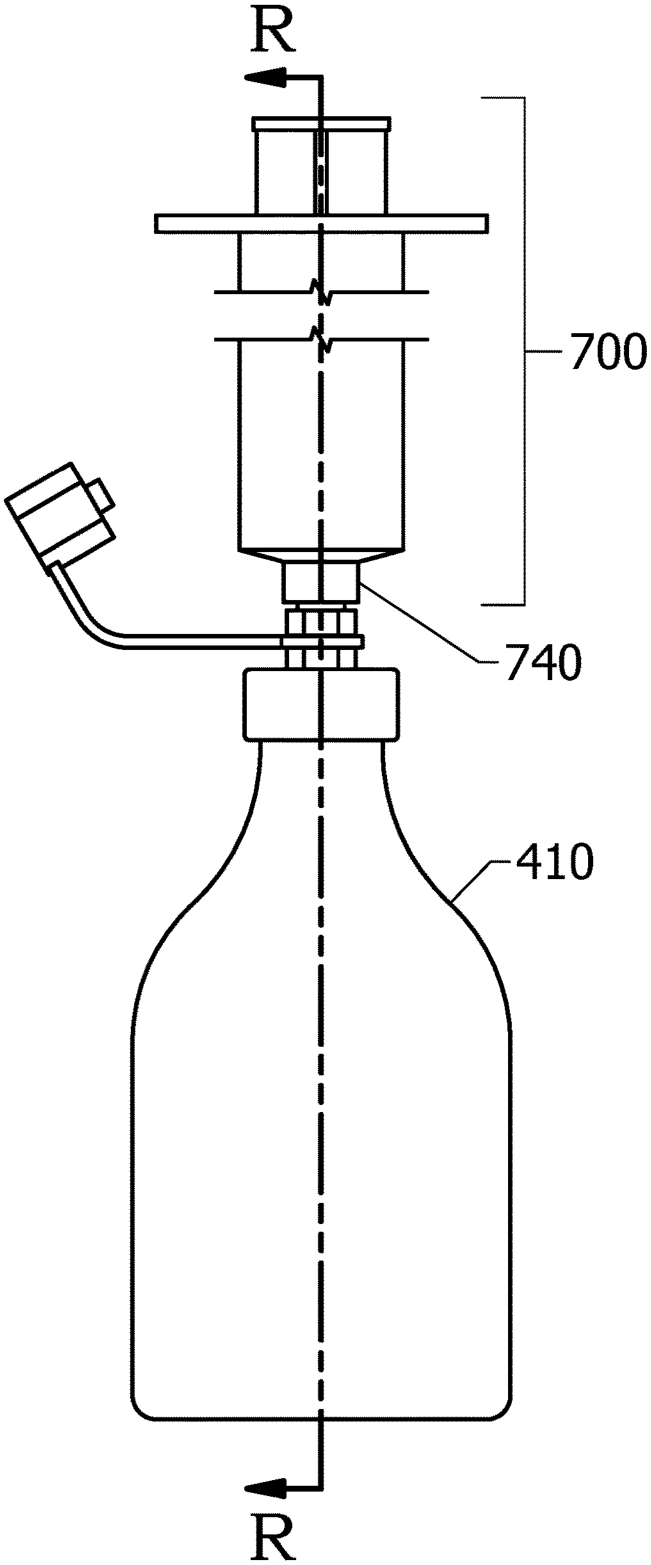
FIG. 18 (comprising FIGS. 18A-18C) depicts further details of the assembly illustrated in FIG. 17, including a side view, a cross-sectional view along an imaginary line depicted using dashes in FIG. 18A, and a close-up view of a portion of the cross-sectional view, respectively.
Figure 18B:
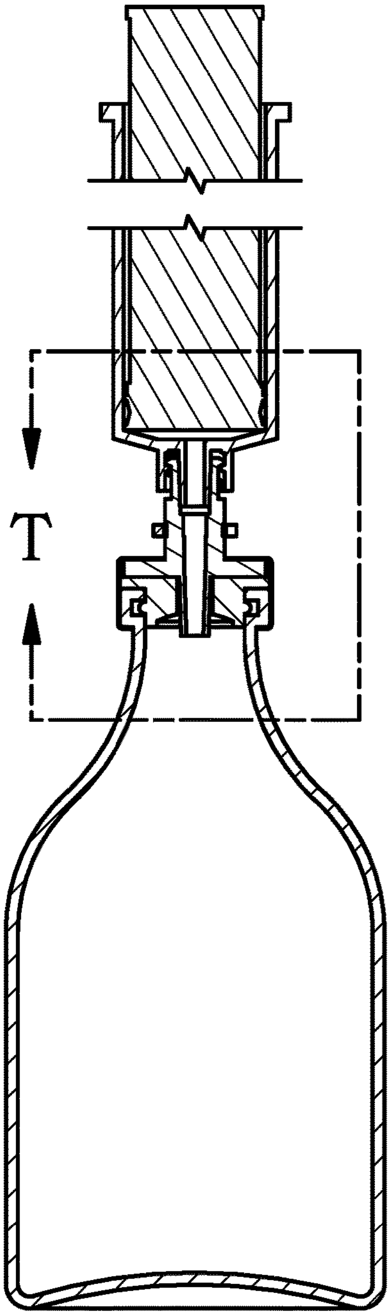
Figure 18C:
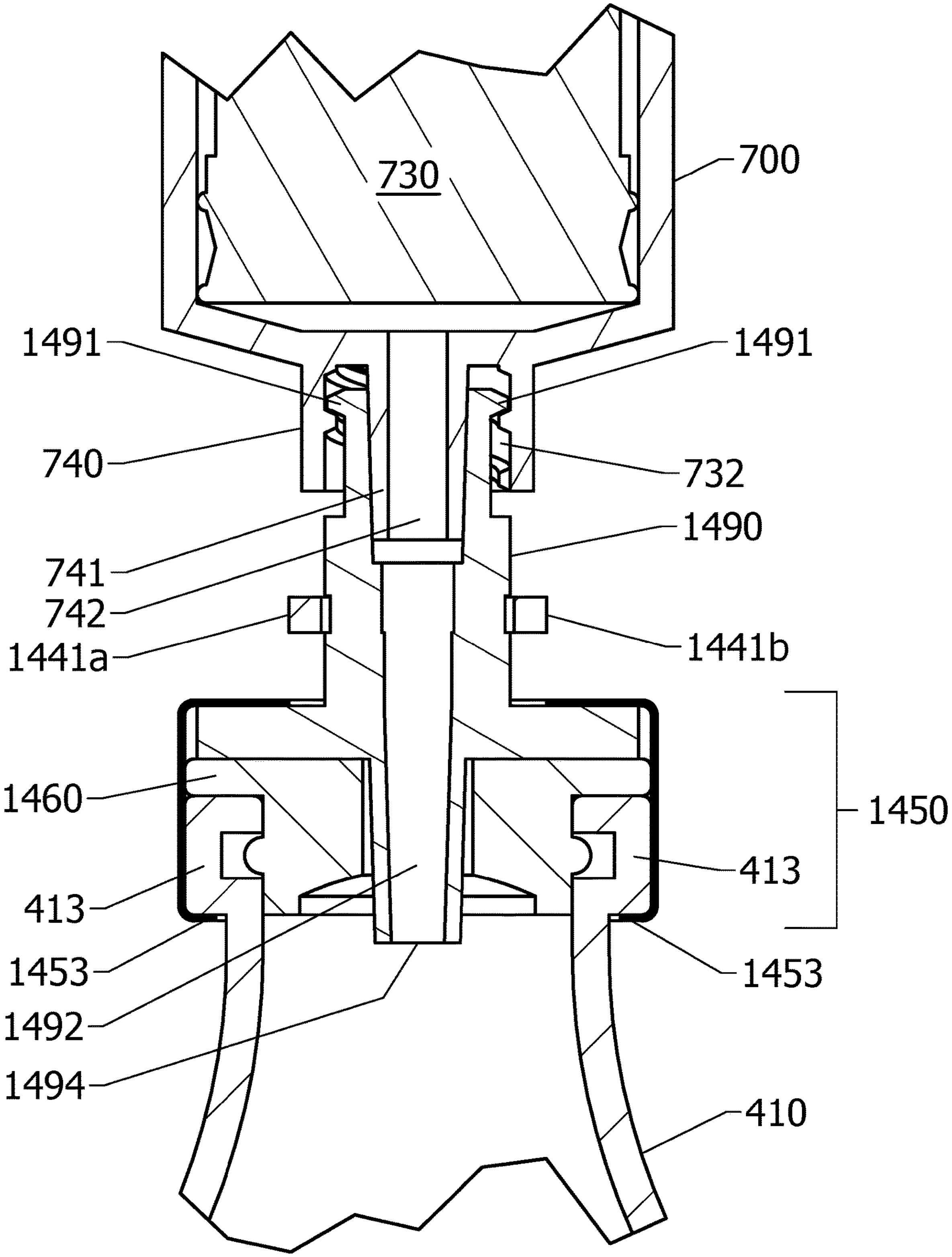

FIG. 18A illustrates a side view of the assembly shown in FIG. 17, with syringe 700 attached to bottle 410. FIG. 18B provides a cross-sectional view along an imaginary line that is denoted as "R" and depicted using dashes in FIG. 18A. FIG. 18C provides a close-up view of a portion of the cross-sectional view of FIG. 18B, this portion denoted as "T" in FIG. 18B, and for ease of reference, discussions will now refer to the close-up view in FIG. 18C.

FIG. 18C shows the component 1450 of the container adapter surrounding neck opening edge 413 and stopper 1460 to thereby secure the container adapter 1420 to the bottle 410 while encapsulating syringe adapter 1490, as has been discussed above with reference to FIG. 15C. FIG. 18C differs from FIG. 15C, however, in that the cap 1430 is now opened and replaced with syringe 700 as noted above with reference to FIG. 17. FIG. 18C shows how syringe 700 is securably attached to syringe adapter 1490, this attachment comprising inserting flanged area 1491 into corresponding internal threads of threaded area 732 shown in the interior of syringe tip 740 and then twisting until flanged area 1491 of the syringe adapter 1490 locks into place within threaded area 732. As can be seen in FIG. 18C, the proximal end of syringe adapter 1490 is preferably sized—as disclosed in one or more of the related applications—so as to slip over the protrusion 741 while at the same time, fitting within the threaded interior area 732 of syringe tip 740. (As noted above and as discussed in one or more of the related applications, inner and outer diameters of the proximal end—i.e., the end where reference number 1491 is generally pointing—are preferably designed for compatibility with such measurements to enable syringe adapter 1490 to make a secure attachment to the internal threaded area 732 of a syringe tip 740 that is manufactured in conformance with measurements provided in the above-cited International Standard ISO 80369-7.)

FIG. 18C depicts, in detail, how a fluid path exists for withdrawing fluid from bottle 410 through the opening 1494 into the syringe adapter 1490, then through the hollow chamber 1492 of the syringe adapter 1490, then through proximal end opening 1497 (shown in FIG. 16) of the syringe adapter where it meets with an opening shown generally at 742 of protrusion 741, and finally into the barrel 730 of syringe 700. Because the disclosed container adapter securably connects all of the elements as illustrated in FIG. 18 (i.e., syringe, syringe adapter, and bottle), a user now has fewer things to hold and to manage during the withdrawal process and may therefore be less likely to experience problems while withdrawing fluid, as was noted earlier.

While illustrations provided for describing embodiments of the present invention show particular shapes and relative dimensions for various components, an embodiment of the present invention is not limited to the shapes and/or dimensions as illustrated. As one example, illustrations in FIGS. 4-18 depict an outer perimeter of component 450, component 950, and component 1450 as being generally round. Embodiments of the present invention are not limited to this shape for the outer perimeter, however; the outer perimeter might alternatively be multi-sided, such as hexagonal, without deviating from the scope of the present invention. An interior perimeter of these components, on the other hand, is preferably round so as to conform to the shape of the collar or neck opening edge at the top of the bottle. (And, if an embodiment of the present invention is used with a bottle having a collar or neck opening edge that is not round, then an interior perimeter of component 450, 950, or 1450 preferably has a shape corresponding generally thereto.)

It should be noted that while discussions herein refer in some cases to making a locking connection by twisting a first feature within a second feature, it will be obvious that the second feature may be twisted within the first feature or that both features may be twisted, without deviating from the scope of the present invention.

An embodiment of the disclosed container adapter is configured, as has been described, to securely hold a syringe adapter in an attachment to a bottle at one end, while allowing the other end of the syringe adapter to be removably connected to a cap and to a syringe. Once the container adapter and its enclosed syringe adapter have been used for withdrawing fluid from a bottle into a syringe, the syringe is removed from this assembly (at some point), and the syringe may then be fitted with a needle so that it is then usable for injecting at least a portion of the withdrawn fluid into a recipient.

The embodiments illustrated in FIGS. 4-18 have been described primarily as container adapters that include, as part of the assembly, a syringe adapter. It will be obvious, in view of the illustrations in FIGS. 4-18 and their accompanying descriptions, that (at least) fourth through sixth embodiments of a container adapter are envisaged and disclosed herein, these embodiments differing from the first through third embodiments by absence of the actual syringe adapter (and absence of corresponding steps in method claims for such embodiments). Referring to FIG. 6, by way of example, a fourth embodiment comprises elements shown at reference number 420 with exception of the syringe adapter 490, where component 450 is adapted for closing around a separately-provided syringe adapter 490. Similarly, with reference to FIG. 11, a fifth embodiment comprises elements shown at reference number 920 with exception of the syringe adapter 990, where component 950 is provided with an open area into which a syringe adapter 990 can be inserted; and with reference to FIG. 16, a sixth embodiment comprises elements shown at reference number 1420 with exception of the syringe adapter 1490. Accordingly, the scope of the present invention includes container adapters that hold a syringe adapter as well as container adapters that are configured for holding, but do not yet hold, a syringe adapter (i.e., where the syringe adapter is to be added to the assembly at a later time).

It should be noted that while embodiments are described herein as conforming to the above-cited International Standards and/or as using Luer-type connections to a syringe, this is by way of illustration but not of limitation. It should also be noted that the figures are directed toward illustrating aspects of the present invention, in combination with descriptions herein, and aspects shown therein (for example, length, width, and/or taper) are not necessarily drawn to scale.

While fluid medications have been discussed herein as commonly being sold in a multi-dose bottle, this is by way of illustration and not of limitation. The disclosed container adapter may be used beneficially for fluid medication that is sold in a single-use dosage.

Advantageously, an embodiment of the disclosed container adapter may be included with purchase (e.g., within the packaging) of a higher-viscosity fluid medication; the disclosed container adapter may also be sold separately from fluid medication. And as noted above, an embodiment of the disclosed container adapter may be provided as a permanent attachment to a bottle. Advantageously, a supplier of packaged container adapters may ensure that they are sterilized and/or sanitized by distributing them in sealed packaging.

As has been demonstrated, an embodiment of the present invention improves a user experience while withdrawing fluid from a container into a syringe, whereby the user no longer needs to hold a bottle and a syringe with attached syringe adapter. Instead, those components are assembled as a single unit by an embodiment of the disclosed container adapter. This is particularly advantageous when withdrawing a viscous fluid, which requires a relatively long draw time and thus introduces more time for user fatigue and/or distraction, which in turn could lead to the user losing his or her grip on the bottle or syringe. This increased ease of use may provide various benefits, including increased sales of viscous fluid medications.

It should be noted that various features discussed herein with reference to "an embodiment", "one embodiment", "a preferred embodiment", and so forth should not be construed as suggesting that each such feature is present in a single embodiment, or in every embodiment, of the present invention. Instead, it should be understood that there may be various combinations of the disclosed features present in any particular embodiment.

While embodiments of the present invention have been described, additional variations and modifications in those embodiments may occur to those of ordinary skill in the art once they learn of the basic inventive concepts. Therefore, it is intended that the appended claims shall be construed to include the described embodiments and all such variations and modifications as fall within the spirit and scope of the invention.

The invention claimed is:

1. A container adapter, comprising:

a component configured for securely attaching a syringe adapter to a fluid-holding container, wherein:

the syringe adapter comprises a sidewall extending continuously and without gaps, as a unitary piece, between a proximal end and a distal end opposite the proximal end, the sidewall having an interior surface defining a chamber, the sidewall defining a proximal-end opening and a distal-end opening at a terminal edge of the proximal end and the distal end, respectively, the proximal end configured to be threadably connectable to a syringe tip at a distal end of a syringe and the distal end configured to be inserted through a covering disposed across a neck opening of the container, the syringe adapter further comprising a lateral extension extending laterally and perpendicularly from an exterior surface of the sidewall, the proximal end of the syringe adapter being positioned proximally from the lateral extension and the distal end of the syringe adapter being positioned distally from the lateral extension;

the component is comprised of a flat uppermost surface with a central bore therethrough, the flat uppermost surface having descending distally therefrom, at an outer circumferential edge, a side portion formed as a plurality of adjacent sides and a plurality of gaps, each of the sides extending continuously and without interruption from the outer circumferential edge to at a distal-most terminal end of the side, each pair of the adjacent sides being separated from one another by a different one of the gaps, each gap extending upward from the distal-most terminal end of the side to the outer circumferential edge, each of the sides being able to flex slightly outward at the distal-most terminal end, each distal-most terminal end formed as an inwardly-extending lip area, the sides together forming a component sidewall of the component;

an underside of the flat uppermost surface and an interior side of the component sidewall together define an inner void of the component; and the component is configured for securely attaching over a collar on the neck opening of the container by flexing the sides over the collar while the syringe adapter extends proximally and distally from the central bore such that the distal end of the syringe adapter extends through the covering and into an interior of the container until the lip area hooks underneath a lower edge of the collar, thereby encapsulating the lateral extension and the collar within the inner void and causing a lowermost surface of the lateral extension to abut, with no intervening structure, a top side of the collar and the covering while an opposing uppermost surface of the lateral extension simultaneously abut the underside of the flat uppermost surface of the component, thereby holding the distal end of the syringe adapter extending distally through the central bore and within the interior of the container and the proximal end of the syringe adapter extending proximally from the flat uppermost surface; and a cap fixedly attached to an exterior of the component sidewall by a lanyard extending therebetween, the cap configured to threadably connect to the proximal end of the syringe adapter and thereby close off the proximal-end opening into the chamber of the syringe adapter, the cap further configured to be threadably disconnectable from the proximal end of the syringe adapter for threadably connecting the syringe tip to the proximal end of the syringe adapter to thereby open the proximal-end opening into the chamber to open a fluid path connecting a barrel of the syringe, the chamber of the syringe adapter, and through the distal-end opening of the syringe adapter, the fluid-holding interior of the container.

2. The container adapter according to claim 1, wherein the cap threadably connects to the proximal end of the syringe adapter using a secure, Luer-type lock connection.

3. The container adapter according to claim 2, wherein the secure, Luer-type lock connection is made by rotating a flanged area extending laterally from the proximal end of the syringe adapter within corresponding internal threads of a threaded area in the cap, the flanged area also configured for making a secure, Luer-type lock connection with the syringe tip.

4. The container adapter according to claim 1, wherein:
an end of the lanyard opposite of the fixed attachment to the component sidewall is configured with a ring-shaped end that surrounds a corresponding ring-receiving portion of the cap and enables the cap to rotate therewithin for the threadable connection to, and threadable disconnection from, the proximal end of the syringe adapter.

5. The container adapter according to claim 1, wherein a topmost portion of each gap extends at least partially into the flat uppermost surface, the topmost portion located opposite the distal-most terminal end of the sides, thereby interrupting continuity of the outer circumferential edge.

6. The container adapter according to claim 1, wherein the secure attachment of the syringe adapter to the container is a permanent attachment.

7. The container adapter according to claim 1, wherein the distal end of the syringe adapter sidewall is frustoconical in exterior shape.

8. A container adapter, comprising:
a component configured for securely holding a syringe adapter while simultaneously securely holding the syringe adapter to a container, wherein:
the component is comprised of a flat uppermost surface with a central bore therethrough, the flat uppermost surface having descending distally therefrom, at an outer circumferential edge, a side portion formed as a plurality of adjacent sides and a plurality of gaps, each of the sides extending continuously and without interruption from the outer circumferential edge to a distal-most terminal end of the side, each pair of the adjacent sides being separated from one another by a different one of the gaps, each gap extending upward from the distal-most terminal end of the side to the outer circumferential edge, each of the sides being able to flex slightly outward at the distal-most terminal end, each distal-most terminal end formed as an inwardly-extending lip area, the sides together forming a component sidewall of the component;
an underside of the flat uppermost surface and an interior side of the component sidewall together define an inner void of the component;
the inner void of the component is configured to encapsulate a lateral extension of the syringe adapter therein, such that a distal end of the syringe adapter extends downwardly through the central bore while a proximal end of the syringe adapter extends upwardly from the flat uppermost surface, the proximal end of the syringe adapter being located opposite the distal end of the syringe adapter, the syringe adapter comprising a sidewall extending continuously and without gaps, as a unitary piece, between the distal end and the proximal end, the lateral extension extending laterally and perpendicularly from an exterior surface of the syringe adapter sidewall, the proximal end of the syringe adapter sidewall defining a proximal-end opening at a terminal end thereof and the distal end of the syringe adapter sidewall defining a distal-end opening at a terminal edge thereof, the distal end configured to insert through a covering disposed across a neck opening of the container; and
the inner void of the component is further configured to securely hold the syringe adapter to the container by simultaneously holding therewithin the lateral extension and a collar on the neck opening of the container, such that a first surface of the lateral extension abuts the underside of the flat uppermost surface while an opposing second surface of the lateral extension abuts a top side of the collar and the covering upon the plurality of sides having flexed outward around an outer circumferential side of the collar until enabling the lip areas to extend inwardly beneath a lower edge of the collar and hook beneath the lower edge as the distal end of the syringe adapter is inserted through the covering, thereby causing the distal end of the syringe adapter to be held within an interior of the container; and
a cap configured for threadably connecting to the proximal end of the syringe adapter using a secure, Luer-type lock connection.

9. The container adapter according to claim 8, wherein:
the cap is fixedly attached to an exterior of the component sidewall by a lanyard extending therebetween; and
an end of the lanyard opposite of the fixed attachment to the component sidewall is configured as a ring-shaped end that surrounds a corresponding ring-receiving portion of the cap and enables the cap to rotate therewithin for the threadable connection to the proximal end of the syringe adapter.

10. The container adapter according to claim 8, wherein:
the interior of the container holds a fluid therein; and
the distal-end opening of the syringe adapter provides an entry point for a fluid communication path between the fluid and an inner chamber of the syringe adapter, the inner chamber defined by an interior surface of the sidewall of the syringe adapter.

11. The container adapter according to claim 10, wherein:
the cap is fixedly attached to an exterior of the component sidewall by a lanyard;
the proximal-end opening provides an exit point for the fluid communication path from the inner chamber; and
the cap is configured to close the exit point upon threadably connecting the cap to the proximal end of the syringe adapter using the secure, Luer-type lock connection thereto.

12. The container adapter according to claim 11, wherein the container adapter is further configured to threadably attach a syringe to the container for withdrawing at least a portion of the fluid from the container and through the entry point, along the fluid communication path and through the exit point and into a barrel of the syringe, upon threadably disconnecting the cap from the proximal end of the syringe adapter and threadably connecting thereto a syringe tip of the syringe, the syringe tip providing an opening that connects the fluid communication path from the exit point to the barrel of the syringe.

13. The container adapter according to claim 8, wherein:
the lip areas are configured to hook beneath the lower edge of the collar upon forcing the component over an exterior of the collar and thereby causing the placement of the lip areas beneath the lower edge.

14. The container adapter according to claim 8, wherein:
the cap is fixedly attached to an exterior of the component sidewall by a lanyard; and
the cap is configured to close off the proximal-end opening when threadably connected to the proximal end of the syringe adapter using the secure, Luer-type lock connection thereto, and to open the proximal-end opening when threadably disconnected therefrom.

15. The container adapter according to claim 8, wherein the lateral extension is substantially uniform in thickness and has a diameter sized to prevent the lateral extension from descending into the neck opening.

16. A container adapter, comprising:

a component configured for securely holding a syringe adapter while simultaneously securely holding the syringe adapter to a container, wherein:

the component is comprised of a flat uppermost surface having descending distally therefrom, at an outer circumferential edge, a side portion formed as a plurality of adjacent sides and a plurality of gaps, each of the sides extending continuously and without interruption from the outer circumferential edge to a distal-most terminal end of the side, each pair of the adjacent sides being separated from one another by a different one of the gaps, each gap extending upward from the distal-most terminal end of the side to the outer circumferential edge, each of the sides being able to flex slightly outward at the distal-most terminal end, each distal-most terminal end formed as an inwardly-extending lip area, the sides together forming a component sidewall of the component;

an underside of the flat uppermost surface and an interior side of the component sidewall together define an inner void of the component;

the flat uppermost surface of the component is configured with a central bore therethrough;

the inner void of the component is configured to encapsulate a lateral extension of the syringe adapter therein upon the insertion through the central bore, such that a distal end of the syringe adapter extends downwardly through the central bore while a proximal end of the syringe adapter extends upwardly from the central bore, the syringe adapter comprising a sidewall extending continuously and without gaps, as a unitary piece, between a terminal edge of the distal end and a terminal edge of the proximal end, the lateral extension extending laterally and perpendicularly from an exterior surface of the syringe adapter sidewall, the proximal end of the syringe adapter being located opposite the distal end of the syringe adapter, the proximal end of the syringe adapter sidewall defining a proximal-end opening at the terminal edge thereof and the distal end of the syringe adapter sidewall defining a distal-end opening at the terminal edge thereof, the distal end configured to insert through a covering disposed across a neck opening of the container; and the inner void of the component is further configured to securely hold the syringe adapter to the container by simultaneously holding therewithin the lateral extension and a collar on the neck opening of the container upon the plurality of sides having flexed outward around an outer circumferential side of the collar until enabling the lip areas to extend inwardly beneath a lower edge of the collar and hook beneath the lower edge as the distal end of the syringe adapter is inserted through the covering, thereby causing the lateral extension to be sandwiched, without other intervening structure, between the underside of the flat uppermost surface and a top side of the collar and the covering while also causing the distal end of the syringe adapter to be held extending distally through the covering and within an interior of the container; and a cap fixedly attached to an exterior of the component sidewall by a lanyard, the cap configured to threadably connect to the proximal end of the syringe adapter, an end of the lanyard opposite of the fixed attachment to the component sidewall configured as a ring-shaped end, the ring-shaped end surrounding a corresponding ring-receiving portion of the cap to thereby enable the cap to rotate therewithin for the threadable connection to the proximal end of the syringe adapter.

17. The container adapter according to claim 16, wherein the cap threadably connects to the proximal end of the syringe adapter using a secure, Luer-type lock connection that is made by rotating a flanged area extending laterally from the proximal end of the syringe adapter within corresponding internal threads of a threaded area in the cap, the flanged area also configured for making a secure, Luer-type lock connection with a syringe tip of a syringe.

18. The container adapter according to claim 16, wherein:

the interior of the container holds a fluid therein;

the distal-end opening of the syringe adapter provides an entry point for a fluid communication path between the fluid and an inner chamber of the syringe adapter, the inner chamber defined by an interior surface of the sidewall of the syringe adapter;

the proximal-end opening provides an exit point for the fluid communication path from the inner chamber; and the cap is configured to close the exit point upon threadably connecting the cap to the proximal end of the syringe adapter using the secure, Luer-type lock connection thereto.

19. The container adapter according to claim 18, wherein the container adapter is further configured to threadably attach a syringe to the container for withdrawing at least a portion of the fluid from the container and through the entry point, along the fluid communication path and through the exit point and into a barrel of the syringe, upon threadably disconnecting the cap from the proximal end of the syringe adapter and threadably connecting thereto a syringe tip of the syringe, the syringe tip providing an opening that connects the fluid communication path from the exit point to the barrel of the syringe.

20. The container adapter according to claim 16, wherein the lateral extension has a diameter sized to prevent entry of the lateral extension into the neck opening.

* * * * *